United States Patent [19]
Sick et al.

[11] Patent Number: 5,426,049
[45] Date of Patent: Jun. 20, 1995

[54] PS176 GENE ENCODING NEMATODE-ACTIVE TOXIN CLONED FROM A BACILLUS THURINGIENSIS ISOLATE

[75] Inventors: August J. Sick, Oceanside; George E. Schwab, La Jolla; Jewel M. Payne, San Diego, all of Calif.

[73] Assignee: Mycogen Corporation, San Diego, Calif.

[21] Appl. No.: 132,739

[22] Filed: Oct. 6, 1993

Related U.S. Application Data

[60] Division of Ser. No. 557,246, Jul. 24, 1990, Pat. No. 5,281,530, which is a continuation-in-part of Ser. No. 535,810, Jun. 11, 1990, abandoned, which is a continuation-in-part of Ser. No. 84,653, Aug. 12, 1987, Pat. No. 4,948,734.

[51] Int. Cl.$^6$ .............. C12N 1/20; C12N 15/00; A01N 63/00
[52] U.S. Cl. .............. 435/252.3; 435/252.33; 435/320.1; 536/23.71; 424/93.461
[58] Field of Search .............. 536/23.71; 435/320.1, 435/252.3, 252.31, 252.33; 530/350; 424/93 L

[56] References Cited

PUBLICATIONS

Haider, et al. *Gene*, 52, pp. 285–290, 1987.
Prefontaine et al. *Appl. Env. Mic.*, vol. 53, No. 12, pp. 2808–2814, Dec. 1987.
Prichard, R. K. et al. (1980) "The Problem of Anthelmintic Resistance in Nematodes" Australian Veterinary Journal 56:239–251.
Coles, G. C. (1986) "Anthelmintic Resistance in Sheep" Veterinary Clinics of North America: Food Animal Practice 2(2):423–432.
Bottjer, K. P., L. W. Bone, S. S. Gill (1985) "Nematoda: Susceptibility of the Egg to *Bacillus thuringiensis* Toxins" Experimental Parasitology 60:239–244.
Ignoffo, C. M., V. H. Dropkin (1977) "Deleterious Effects of the Thermostable Toxin of *Bacillus thuringiensis* on Species of Soil–Inhabiting, Myceliophagus, and Plant Parasitic Nematodes" Journal of the Kansas Entomological Society 50(3):394–398.
Ciordia, H., W. E. Bizzell (1961) "A Prelinary Report of the Effects of *Bacillus thuringiensis* var. *thuringiensis* Berliner on the Development of the Free-living Stages of Some Cattle Nematodes" Journal of Parasitology 47:41, abstract no. 86.

*Primary Examiner*—Robert A. Wax
*Assistant Examiner*—Keith D. Hendricks
*Attorney, Agent, or Firm*—Saliwanchik & Saliwanchik

[57] ABSTRACT

Nematicidal δ-endotoxin encoding genes have been cloned from a novel *Bacillus thuringiensis* isolate known as *B.t.* PS17. These novel genes, designated *B.t.* PS17a, *B.t.* PS17b, *B.t.* PS17d, and *B.t.* PS17e, can be transferred to various microbial and plant hosts via known techniques. In the microbial or plant host, one or more of the genes of the invention can be used to express the novel nematicidal toxins to control susceptible nematodes.

4 Claims, 34 Drawing Sheets

```
Met Ala Ile Leu Asn Glu Leu Tyr Pro Ser Val Pro Tyr Asn Val Leu
1               5                   10                  15
Ala Tyr Thr Pro Pro Ser Phe Leu Pro Asp Ala Gly Thr Gln Ala Thr
            20              25                  30
Pro Ala Asp Leu Thr Ala Tyr Glu Gln Leu Leu Lys Asn Leu Glu Lys
        35              40              45
Gly Ile Asn Ala Gly Thr Tyr Ser Lys Ala Ile Ala Asp Val Leu Lys
    50              55              60
Gly Ile Phe Ile Asp Asp Thr Ile Asn Tyr Gln Thr Tyr Val Asn Ile
65              70              75                      80
Gly Leu Ser Leu Ile Thr Leu Ala Val Pro Glu Ile Gly Ile Phe Thr
            85              90              95
Pro Phe Ile Gly Leu Phe Phe Ala Ala Leu Asn Lys His Asp Ala Pro
            100             105             110
Pro Pro Pro Asn Ala Lys Asp Ile Phe Glu Ala Met Lys Pro Ala Ile
        115             120             125
Gln Glu Met Ile Asp Arg Thr Leu Thr Ala Asp Glu Gln Thr Phe Leu
    130             135             140
Asn Gly Glu Ile Ser Gly Leu Gln Asn Leu Ala Ala Arg Tyr Gln Ser
145             150             155             160
Thr Met Asp Asp Ile Gln Ser His Gly Gly Phe Asn Lys Val Asp Ser
            165             170             175
Gly Leu Ile Lys Lys Phe Thr Asp Glu Val Leu Ser Leu Asn Ser Phe
        180             185             190
Tyr Thr Asp Arg Leu Pro Val Phe Ile Thr Asp Asn Thr Ala Asp Arg
        195             200             205
Thr Leu Leu Gly Leu Pro Tyr Tyr Ala Ile Leu Ala Ser Met His Leu
    210             215             220
Met Leu Leu Arg Asp Ile Ile Thr Lys Gly Pro Thr Trp Asp Ser Lys
225             230             235             240
Ile Asn Phe Thr Pro Asp Ala Ile Asp Ser Phe Lys Thr Asp Ile Lys
            245             250             255
Asn Asn Ile Lys Leu Tyr Ser Lys Thr Ile Tyr Asp Val Phe Gln Lys
        260             265             270
Gly Leu Ala Ser Tyr Gly Thr Pro Ser Asp Leu Glu Ser Phe Ala Lys
    275             280             285
Lys Gln Lys Tyr Ile Glu Ile Met Thr Thr His Cys Leu Asp Phe Ala
    290             295             300
Arg Leu Phe Pro Thr Phe Asp Pro Asp Leu Tyr Pro Thr Gly Ser Gly
305             310             315             320
Asp Ile Ser Leu Gln Lys Thr Arg Arg Ile Leu Ser Pro Phe Ile Pro
            325             330             335
Ile Arg Thr Ala Asp Gly Leu Thr Leu Asn Asn Thr Ser Ile Asp Thr
        340             345             350
Ser Asn Trp Pro Asn Tyr Glu Asn Gly Asn Gly Ala Phe Pro Asn Pro
        355             360             365
Lys Glu Arg Ile Leu Lys Gln Phe Lys Leu Tyr Pro Ser Trp Arg Ala
    370             375             380
Gly Gln Tyr Gly Gly Leu Leu Gln Pro Tyr Leu Trp Ala Ile Glu Val
385             390             395             400
Gln Asp Ser Val Glu Thr Arg Leu Tyr Gly Gln Leu Pro Ala Val Asp
        405             410             415
Pro Gln Ala Gly Pro Asn Tyr Val Ser Ile Asp Ser Ser Asn Pro Ile
        420             425             430
Ile Gln Ile Asn Met Asp Thr Trp Lys Thr Pro Pro Gln Gly Ala Ser
    435             440             445
Gly Trp Asn Thr Asn Leu Met Arg Gly Ser Val Ser Gly Leu Ser Phe
    450             455             460
Leu Gln Arg Asp Gly Thr Arg Leu Ser Ala Gly Met Gly Gly Gly Phe
465             470             475             480
```

Figure 1A

```
Ala Asp Thr Ile Tyr Ser Leu Pro Ala Thr His Tyr Leu Ser Tyr Leu
            485             490                 495
Tyr Gly Thr Pro Tyr Gln Thr Ser Asp Asn Tyr Ser Gly His Val Gly
        500             505                 510
Ala Leu Val Gly Val Ser Thr Pro Gln Glu Ala Thr Leu Pro Asn Ile
        515             520                 525
Ile Gly Gln Pro Asp Glu Gln Gly Asn Val Ser Thr Met Gly Phe Pro
    530             535                 540
Phe Glu Lys Ala Ser Tyr Gly Gly Thr Val Val Lys Glu Trp Leu Asn
545             550             555                 560
Gly Ala Asn Ala Met Lys Leu Ser Pro Gly Gln Ser Ile Gly Ile Pro
                565             570                 575
Ile Thr Asn Val Thr Ser Gly Glu Tyr Gln Ile Arg Cys Arg Tyr Ala
            580             585                 590
Ser Asn Asp Asn Thr Asn Val Phe Phe Asn Val Asp Thr Gly Gly Ala
        595             600                 605
Asn Pro Ile Phe Gln Gln Ile Asn Phe Ala Ser Thr Val Asp Asn Asn
    610             615                 620
Thr Gly Val Gln Gly Ala Asn Gly Val Tyr Val Val Lys Ser Ile Ala
625             630             635                 640
Thr Thr Asp Asn Ser Phe Thr Glu Ile Pro Ala Lys Thr Ile Asn Val
            645             650                 655
His Leu Thr Asn Gln Gly Ser Ser Asp Val Phe Leu Asp Arg Ile Glu
            660             665                 670
Phe Ile Pro Phe Ser Leu Pro Leu Ile Tyr His Gly Ser Tyr Asn Thr
        675             680                 685
Ser Ser Gly Ala Asp Asp Val Leu Trp Ser Ser Ser Asn Met Asn Tyr
    690             695                 700
Tyr Asp Ile Ile Val Asn Gly Gln Ala Asn Ser Ser Ser Ile Ala Ser
705             710             715                 720
Ser Met His Leu Leu Asn Lys Gly Lys Val Ile Lys Thr Ile Asp Ile
                725             730                 735
Pro Gly His Ser Glu Thr Phe Phe Ala Thr Phe Pro Val Pro Glu Gly
            740             745                 750
Phe Asn Glu Val Arg Ile Leu Ala Gly Leu Pro Glu Val Ser Gly Asn
        755             760                 765
Ile Thr Val Gln Ser Asn Asn Pro Pro Gln Pro Ser Asn Asn Gly Gly
    770             775                 780
Gly Asp Gly Gly Gly Asn Gly Gly Gly Asp Gly Gly Gln Tyr Asn Phe
785             790             795                 800
Ser Leu Ser Gly Ser Asp His Thr Thr Ile Tyr His Gly Lys Leu Glu
            805             810                 815
Thr Gly Ile His Val Gln Gly Asn Tyr Thr Tyr Thr Gly Thr Pro Val
            820             825                 830
Leu Ile Leu Asn Ala Tyr Arg Asn Asn Thr Val Val Ser Ser Ile Pro
        835             840                 845
Val Tyr Ser Pro Phe Asp Ile Thr Ile Gln Thr Glu Ala Asp Ser Leu
    850             855                 860
Glu Leu Glu Leu Gln Pro Arg Tyr Gly Phe Ala Thr Val Asn Gly Thr
865             870             875                 880
Ala Thr Val Lys Ser Pro Asn Val Asn Tyr Asp Arg Ser Phe Lys Leu
                885             890                 895
Pro Ile Asp Leu Gln Asn Ile Thr Thr Gln Val Asn Ala Leu Phe Ala
            900             905                 910
Ser Gly Thr Gln Asn Met Leu Ala His Asn Val Ser Asp His Asp Ile
            915             920                 925
Glu Glu Val Val Leu Lys Val Asp Ala Leu Ser Asp Glu Val Phe Gly
        930             935                 940
Asp Glu Lys Lys Ala Leu Arg Lys Leu Val Asn Gln Ala Lys Arg Leu
945             950             955                 960
Ser Arg Ala Arg Asn Leu Leu Ile Gly Gly Ser Phe Glu Asn Trp Asp
                965             970                 975
Ala Trp Tyr Lys Gly Arg Asn Val Val Thr Val Ser Asp His Glu Leu
            980             985                 990
```

Figure 1B

```
Phe Lys Ser Asp His Val Leu Leu Pro Pro Pro Gly Leu Ser Pro Ser
         995                 1000                1005
Tyr Ile Phe Gln Lys Val Glu Glu Ser Lys Leu Lys Pro Asn Thr Arg
    1010                1015                1020
Tyr Ile Val Ser Gly Phe Ile Ala His Gly Lys Asp Leu Glu Ile Val
1025                1030                1035                1040
Val Ser Arg Tyr Gly Gln Glu Val Gln Lys Val Val Gln Val Pro Tyr
            1045                1050                1055
Gly Glu Ala Phe Pro Leu Thr Ser Asn Gly Pro Val Cys Cys Pro Pro
                1060                1065            1070
Arg Ser Thr Ser Asn Gly Thr Leu Gly Asp Pro His Phe Phe Ser Tyr
        1075                1080                1085
Ser Ile Asp Val Gly Ala Leu Asp Leu Gln Ala Asn Pro Gly Ile Glu
    1090                1095                1100
Phe Gly Leu Arg Ile Val Asn Pro Thr Gly Met Ala Arg Val Ser Asn
1105                1110                1115                1120
Leu Glu Ile Arg Glu Asp Arg Pro Leu Ala Ala Asn Glu Ile Arg Gln
                1125                1130                1135
Val Gln Arg Val Ala Arg Asn Trp Arg Thr Glu Tyr Glu Lys Glu Arg
            1140                1145                1150
Ala Glu Val Thr Ser Leu Ile Gln Pro Val Ile Asn Arg Ile Asn Gly
        1155                1160                1165
Leu Tyr Glu Asn Gly Asn Trp Asn Gly Ser Ile Arg Ser Asp Ile Ser
    1170                1175                1180
Tyr Gln Asn Ile Asp Ala Ile Val Leu Pro Thr Leu Pro Lys Leu Arg
1185                1190                1195                1200
His Trp Phe Met Ser Asp Arg Phe Ser Glu Gln Gly Asp Ile Met Ala
                1205                1210                1215
Lys Phe Gln Gly Ala Leu Asn Arg Ala Tyr Ala Gln Leu Glu Gln Ser
            1220                1225                1230
Thr Leu Leu His Asn Gly His Phe Thr Lys Asp Ala Ala Asn Trp Thr
        1235                1240                1245
Ile Glu Gly Asp Ala His Gln Ile Thr Leu Glu Asp Gly Arg Arg Val
    1250                1255                1260
Leu Arg Leu Pro Asp Trp Ser Ser Ser Val Ser Gln Met Ile Glu Ile
1265                1270                1275                1280
Glu Asn Phe Asn Pro Asp Lys Glu Tyr Asn Leu Val Phe His Gly Gln
                1285                1290                1295
Gly Glu Gly Thr Val Thr Leu Glu His Gly Glu Glu Thr Lys Tyr Ile
            1300                1305                1310
Glu Thr His Thr His His Phe Ala Asn Phe Thr Thr Ser Gln Arg Gln
        1315                1320                1325
Gly Leu Thr Phe Glu Ser Asn Lys Val Thr Val Thr Ile Ser Ser Glu
    1330                1335                1340
Asp Gly Glu Phe Leu Val Asp Asn Ile Ala Leu Val Glu Ala Pro Leu
1345                1350                1355                1360
Pro Thr Asp Asp Gln Asn Ser Glu Gly Asn Thr Ala Ser Ser Thr Asn
                1365                1370                1375
Ser Asp Thr Ser Met Asn Asn Asn Gln
        1380                1385
```

Figure 1C

| | | | | | |
|---|---|---|---|---|---|
| ATGGCAATTT | TAAATGAATT | ATATCCATCT | GTACCTTATA | ATGTATTGGC | GTATACGCCA | 60 |
| CCCTCTTTTT | TACCTGATGC | GGGTACACAA | GCTACACCTG | CTGACTTAAC | AGCTTATGAA | 120 |
| CAATTGTTGA | AAAATTTAGA | AAAAGGGATA | AATGCTGGAA | CTTATTCGAA | AGCAATAGCT | 180 |
| GATGTACTTA | AAGGTATTTT | TATAGATGAT | ACAATAAATT | ATCAAACATA | TGTAAATATT | 240 |
| GGTTTAAGTT | TAATTACATT | AGCTGTACCG | GAAATTGGTA | TTTTTACACC | TTTCATCGGT | 300 |
| TTGTTTTTG | CTGCATTGAA | GCTCCACCTC | TAAACATGAT | CTCCTAATGC | AAAAGATATA | 360 |
| TTTGAGGCTA | TGAAACCAGC | GATTCAAGAG | ATGATTGATA | GAACTTAAC | TGCGGATGAG | 420 |
| CAAACATTT | TAAATGGGGA | AATAAGTGT | TTACAAAAT | TAGCAGCAAG | ATACCAGTCT | 480 |
| ACAATGGATG | ATATTCAAAG | CCATGGAGGA | TTTAATAAGG | TAGATTCTGG | ATTAATTAAA | 540 |
| AAGTTACAG | ATGAGGTACT | ATCTTTAAAT | AGTTTTTATA | CAGATCGTTT | ACCTGTATTT | 600 |
| ATTACAGATA | ATACAGCGGA | TCGAACTTTG | TTAGGTCTTC | CTTATTATGC | TATACTTGCG | 660 |
| AGCATGCATC | TTATGTTATT | AAGAGATATC | ATTACTAAGG | GTCCGACATG | GGATTCTAAA | 720 |
| ATTAATTTCA | CACCAGATGC | AATTGATTCC | TTTAAAACCG | ATATTAAAAA | TAATATAAAG | 780 |
| CTTTACTCTA | AAACTATTTA | TGACGTATTT | CAGAAGGGAC | TTGCTTCATA | CGGAACGCCT | 840 |
| TCTGATTTAG | AGTCCTTTGC | AAAAAAACAA | TCCTACTTT | GATCCAGATC | AAATTATGAC | AACACATTGT | 900 |
| TTAGATTTTG | CAAGATTGTT | TACAAAAAAC | ACGTAGAATT | CTTTCTCCTT | TTATCCCTAT | ACGTACTGCA | 960 |
| GATATAAGTT | TACAAAATAA | TACTTCAATT | GATACTTCAA | ATTGGCCTAA | TTATGAAAAT | 1020 |
| GATGGGTTAA | CATTAAATAA | CCCAAAAGAA | AGAATATTAA | AACAATTCAA | ACTGTATCCT | 1080 |
| GGGAATGGCG | CGTTTCCAAA | CGGTGGGCTT | TTACAACCTT | ATTTATGGGC | AATAGAAGTC | 1140 |
| AGTTGGAGAG | CGGGACAGTA | | | | | 1200 |

Figure 2A

| | | | | |
|---|---|---|---|---|
| CAAGATTCTG | TAGAGACTCG | TTTGTATGGG | CAGCTTCCAG | CTGTAGATCC | ACAGGCAGGG | 1260 |
| CCTAATTATG | TTTCCATAGA | TTCTTCTAAT | CCAATCATAC | AAATAAATAT | GGATACTTGG | 1320 |
| AAACACCAC | CACAAGGTGC | GAGTGGGTGG | AATACAAATT | TAATGAGAGG | AAGTGTAAGC | 1380 |
| GGGTTAAGTT | TTTTACAACG | AGATGGTACG | AGACTTAGTG | CTGGTATGGG | TGGTGGTTTT | 1440 |
| GCTGATACAA | TATATAGTCT | CCCTGCAACT | CATTATCTTT | CTTATCTCTA | TGGAACTCCT | 1500 |
| TATCAAACTT | CTGATAACTA | TTCTGGTCAC | GTTGGTGCAT | TGGTAGGTGT | GAGTACGCCT | 1560 |
| CAAGAGGCTA | CTCTTCCTAA | TATTATAGGT | CAACCAGATG | AACAGGGAAA | TGTATCTACA | 1620 |
| ATGGGATTTC | CGTTTGAAAA | AGCTTCTTAT | GGAGGTACAG | TTGTTAAAGA | ATGGTTAAAT | 1680 |
| GGTGCGAATG | CGATGAAGCT | TTCTCCTGGG | CAATCTATAG | GTATTCCTAT | TACAAATGTA | 1740 |
| ACAAGTGGAG | AATATCAAAT | TCGTTGTCGT | TATGCAAGTA | ATGATAATAC | TAACGTTTTC | 1800 |
| TTTAATGTAG | ATACTGGTGG | AGCAAATCCA | ATTTTCCAAC | AGATAAACTT | TGCATCTACT | 1860 |
| GTAGATAATA | ATACGGGAGT | ACAAGGAGCA | AATGGTGTCT | ATGTAGTCAA | ATCTATTGCT | 1920 |
| ACAACTGATA | ATTCTTTTAC | AGAAATTCCT | GCGAAGACGA | TTAATGTTCA | TTTAACCAAC | 1980 |
| CAAGGTTCTT | CTGATGTCTT | TTTAGACCGT | ATTGAATTTA | TACCTTTTTC | TCTACCTCTT | 2040 |
| ATATATCATG | GAAGTTATAA | TACTTCATCA | GGTGCAGATG | ATGTTTTATG | GTCTTCTTCA | 2100 |
| AATATGAATT | ACTACGATAT | AATAGTAAAT | GGTCAGGCCA | ATAGTAGTAG | TATCGCTAGT | 2160 |
| TCTATGCATT | TGCTTAATAA | AGGAAAAGTG | ATAAAAACAA | TTGATATTCC | AGGGCATTCG | 2220 |
| GAAACCTTCT | TTGCTACGTT | CCCAGTTCCA | GAAGGATTTA | ATGAAGTTAG | AATTCTTGCT | 2280 |
| GGCCTTCCAG | AAGTTAGTGG | AAATATTACC | GTACAATCTA | ATAATCCGCC | TCAACCTAGT | 2340 |
| AATAATGGTG | GTGGTGATGG | TGGTGGTAAT | GGTGGTGGTG | ATGGTGGTCA | ATACAATTTT | 2400 |

Figure 2B

```
TCTTTAAGCG GATCTGATCA TACGACTATT TATCATGGAA AACTTGAAAC TGGGATTCAT   2460
GTACAAGGTA ATTATACCTA TACAGGTACT CCCGTATTAA TACTGAATGC TTACAGAAAT   2520
AATACTGTAG TATCAAGCAT TCCAGTATAT TCTCCTTTTG ATATAACTAT ACAGACAGAA   2580
GCTGATAGCC TTGAGCTTGA ACTACAACCT AGATATGGTT TTGCCACAGT GAATGGTACT   2640
GCAACAGTAA AAAGTCCTAA TGTAAATTAC GATAGATCAT TTAAACTCCC AATAGACTTA   2700
CAAAATATCA CAACACAAGT AAATGCATTA TTCGCATCTG GAACACAAAA TATGCTTGCT   2760
CATAATGTAA GTGATCATGA TATTGAAGAA GTTGTATTAA AAGTGGATGC CTTATCAGAT   2820
GAAGTATTTG GAGATGAGAA GAAGGCTTTA CGTAAATTGG TGAATCAAGC AAAACGTTTG   2880
AGTAGAGCAA GAAATCTTCT GATAGGTGGG AGTTTTGAAA ATTGGGATGC ATGGTATAAA   2940
GGAAGAAATG TAGTAACTGT ATCTGATCAT GAACTATTTA AGAGTGATCA TGTATTATTA   3000
CCACCACCAG GATTGTCTCC ATCTTATATT TTCCAAAAAG TGGAGGAATC TAAATTAAAA   3060
CCAAATACAC GTTATATTGT TTCTGGATTC ATCGCACATG GAAAAGACCT AGAAATTGTT   3120
GTTTCACGTT ATGGGCAAGA AGTGCAAAAG GTCGTGCAAG TTCCTTATGG AGAAGCATTC   3180
CCGTTAACAT CAAATGGACC AGTTTGTTGT CCCCCACGTT CTACAAGTAA TGGAACCTTA   3240
GGAGATCCAC ATTTCTTTAG GATGTAGGTG CACTAGATTT ACAAGCAAAC   3300
CCTGGTATTG AATTGGTCT TCGTATTGTA AATCCAACTG GAATGGCACG CGTAAGCAAT   3360
TTGGAAATTC GTGAAGATCG TCCATTAGCA GCAAATGAAA TACGACAAGT ACAACGTGTC   3420
GCAAGAAATT GGAGAACCGA GTATGAGAAA GAACGTGCGG AAGTAACAAG TTTAATTCAA   3480
CCTGTTATCA ATCGAATCAA CGGATTGTAT GAAAATGGAA ATTGGAACGG TTCTATTCGT   3540
```

Figure 2C

```
TCAGATATTT CGTATCAGAA TATAGACGCG ATTGTATTAC CAACGTTACC AAAGTTACGC   3600
CATTGGTTTA TGTCAGATAG ATTCAGTGAA CAAGGAGATA TAATGGCTAA ATTCCAAGGT   3660
GCATTAAATC GTGCGTATGC ACAACTGGAA CAAAGTACGC TTCTGCATAA TGGTCATTTT   3720
ACAAAAGATG CAGCTAATTG GACAATAGAA GGCGATGCAC ATCAGATAAC ACTAGAAGAT   3780
GGTAGACGTG TATTGCGACT TCCAGATTGG TCTTCGAGTG TATCTCAAAT GATTGAAATC   3840
GAGAATTTTA ATCCAGATAA AGAATACAAC TTAGTATTCC ATGGGCAAGG AGAAGGAACG   3900
GTTACGTTGG AGCATGGAGA AGAAACAAAA TATATAGAAA CGCATACACA TCATTTTGCG   3960
AATTTTACAA CTTCTCAACG TCAAGGACTC ACGTTTGAAT CAAATAAAGT GACAGTGACC   4020
ATTTCTTCAG AAGATGGAGA ATTCTTAGTG GATAATATTG CGCTTGTGGA AGCTCCTCTT   4080
CCTACAGATG ACCAAAATTC TGAGGGAAAT ACGGCTTCCA GTACGAATAG CGATACAAGT   4140
ATGAACAACA ATCAA                                                   4155
```

Figure 2D

```
      Met Ala Ile Leu Asn Glu Leu Tyr Pro Ser Val Pro Tyr Asn Val Leu Ala Tyr Thr Pro
      ATG GCA ATT TTA AAT GAA TTA TAT CCA TCT GTA CCT TAT AAT GTA TTG GCG TAT ACG CCA
                        5                  10                  15                  20

Pro Ser Phe Leu Pro Asp Ala Gly Thr Gln Ala Thr Pro Ala Asp Leu Thr Ala Tyr Glu
      CCC TCT TTT TTA CCT GAT GCG GGT ACA CAA GCT ACA CCT GCT GAC TTA ACA GCT TAT GAA
                       25                  30                  35                  40

Gln Leu Leu Lys Asn Leu Glu Lys Gly Ile Asn Ala Gly Thr Tyr Ser Lys Ala Ile Ala
      CAA TTG TTG AAA AAT TTA GAA AAA GGG ATA AAT GCT GGA ACT TAT TCG AAA GCA ATA GCT
                       45                  50                  55                  60

Asp Val Leu Lys Gly Ile Phe Ile Asp Thr Ile Asn Tyr Gln Thr Tyr Val Asn Ile
      GAT GTA CTT AAA GGT ATT TTT ATA GAT ACT ACA AAT TAT CAA ACA TAT GTA AAT ATT
                       65                  70                  75                  80

Gly Leu Ser Leu Ile Thr Leu Ala Val Pro Glu Ile Gly Ile Phe Thr Pro Phe Ile Gly
      GGT TTA AGT TTA ATT ACA TTA GCT GTA CCG GAA ATT GGT ATT TTT ACA CCT TTC ATC GGT
                       85                  90                  95                 100

Leu Phe Phe Ala Leu Asn Lys His Asp Ala Pro Pro Pro Asn Ala Lys Asp Ile
      TTG TTT TTT GCT TTG AAT AAA CAT GAT GCT CCT CCT CCT AAT GCA AAA GAT ATA
                      105                 110                 115                 120
```

Figure 3A

```
            125                 130                 135                 140
Phe Glu Ala Met Lys Pro Ala Ile Gln Glu Met Ile Asp Arg Thr Leu Thr Ala Asp Glu
TTT GAG GCT ATG AAA CCA GCG ATT CAA GAG ATG ATT GAT AGA ACT TTA ACT GCG GAT GAG 145                 150                 155                 160
Gln Thr Phe Leu Asn Gly Glu Ile Ser Gly Leu Gln Asn Leu Ala Ala Arg Tyr Gln Ser
CAA ACA TTT TTA AAT GGG GAA ATA AGT GGT TTA CAA AAT TTA GCA GCA AGA TAC CAG TCT 165                 170                 175                 180
Thr Met Asp Asp Ile Gln Ser His Gly Gly Phe Asn Lys Val Asp Ser Gly Leu Ile Lys
ACA ATG GAT GAT ATT CAA AGC CAT GGA GGA TTT AAT AAG GTA GAT TCT GGA TTA ATT AAA 185                 190                 195                 200
Lys Phe Thr Asp Glu Val Leu Ser Leu Asn Ser Phe Tyr Thr Asp Arg Leu Pro Val Phe
AAG TTT ACA GAT GAG GTA CTA TCT TTA AAT AGT TTT TAT ACA GAT CGT TTA CCT GTA TTT 205                 210                 215                 220
Ile Thr Asp Asn Thr Ala Asp Arg Thr Leu Leu Gly Leu Leu Pro Tyr Tyr Ala Ile Leu Ala
ATT ACA GAT AAT ACA GCG GAT CGA ACT TTG TTA GGT CTT CCT TAT TAT GCT ATA CTT GCG 225                 230                 235                 240
Ser Met His Leu Met Leu Leu Arg Asp Ile Ile Thr Lys Gly Pro Thr Trp Asp Ser Lys
AGC ATG CAT CTT ATG TTA TTA AGA GAT ATC ATT ACT AAG GGT CCG ACA TGG GAT TCT AAA
```

Figure 3B

```
        245                         250                         255                         260
Ile Asn Phe Thr Pro Asp Ala Ile Asp Ser Phe Lys Thr Asp Ile Lys Asn Asn Ile Lys
ATT AAT TTC ACA CCA GAT GCA ATT GAT TCC TTT AAA ACC GAT ATT AAA AAT AAT ATA AAG 265                         270                         275                         280
Leu Tyr Ser Lys Thr Ile Tyr Asp Val Phe Gln Lys Gly Leu Ala Ser Tyr Gly Thr Pro
CTT TAC TCT AAA ACT ATT GAC GTA TTT CAG AAG GGA CTT GCT TCA TAC GGA ACG CCT
                        285                         290                         295          300

Ser Asp Leu Glu Ser Phe Ala Lys Lys Tyr Ile Gln Lys Tyr Ile Glu Ile Met Thr Thr His Cys
TCT GAT TTA GAG TCC TTT GCA AAA AAA TAT ATT GAA ATT ATG ACA ACA CAT TGT
            305                         310                         315                         320

Leu Asp Phe Ala Arg Leu Phe Pro Thr Phe Asp Pro Asp Leu Tyr Pro Thr Gly Ser Gly
TTA GAT TTT GCA AGA TTG TTT CCT ACT TTT GAT CCA GAT CTT TAT CCA ACA GGA TCA GGT
                    325                         330                         335          340

Asp Ile Ser Leu Gln Lys Thr Arg Arg Ile Leu Ser Pro Phe Ile Pro Ile Arg Thr Ala
GAT ATA AGT TTA CAA AAA ACA CGT AGA ATT CTT TCT CCT TTT ATC CCT ATA CGT ACT GCA
            345                         350                         355          360

Asp Gly Leu Thr Leu Asn Asn Thr Ser Ile Asp Thr Ser Asn Trp Pro Asn Tyr Glu Asn
GAT GGG TTA ACA TTA AAT AAT ACT TCA ATT GAT ACT TCA AAT TGG CCT AAT TAT GAA AAT
```

Figure 3C

```
                    365                         370                         375                         380
Gly Asn Gly Ala Phe Pro Asn Pro Lys Glu Arg Ile Leu Lys Gln Phe Lys Leu Tyr Pro
GGG AAT GGC GCG TTT CCA AAC CCA AAA GAA AGA ATA TTA AAA CAA TTC AAA CTG TAT CCT 385                         390                         395                         400
Ser Trp Arg Ala Gly Gln Tyr Gly Gly Leu Leu Gln Pro Tyr Leu Trp Ala Ile Glu Val
AGT TGG AGA GCG GGA CAG TAC GGT GGG CTT TTA CAA CCT TAT TTA TGG GCA ATA GAA GTC 405                         410                         415                         420
Gln Asp Ser Val Glu Thr Arg Leu Tyr Gly Gln Leu Pro Ala Val Asp Pro Gln Ala Gly
CAA GAT TCT GTA GAG ACT CGT TTG TAT GGG CAG CTT CCA GCT GTA GAT CCA CAG GCA GGG 425                         430                         435                         440
Pro Asn Tyr Val Ser Ile Asp Ser Ser Asn Pro Ile Ile Gln Ile Asn Met Asp Thr Trp
CCT AAT TAT GTT TCC ATA GAT TCT TCT AAT CCA ATC ATA CAA ATA AAT ATG GAT ACT TGG 445                         450                         455                         460
Lys Thr Pro Pro Gln Gly Ala Ser Gly Trp Asn Thr Asn Leu Met Arg Gly Ser Val Ser
AAA ACA CCA CCA CAA GGT GCG AGT GGG TGG AAT ACA AAT TTA ATG AGA GGA AGT GTA AGC 465                         470                         475                         480
Gly Leu Ser Phe Leu Gln Arg Asp Gly Thr Arg Leu Ser Ala Gly Met Gly Gly Gly Phe
GGG TTA AGT TTT TTA CAA CGA GAT GGT ACG AGA CTT AGT GCT GGT ATG GGT GGT GGT TTT
```

Figure 3D

```
              485                 490                 495                 500
Ala Asp Thr Ile Tyr Ser Leu Pro Ala Thr His Tyr Leu Ser Tyr Leu Tyr Gly Thr Pro
GCT GAT ACA ATA TAT AGT CTC CCT GCA ACT CAT TAT CTC TCT TAT CTC TAT GGA ACT CCT 505                 510                 515                 520
Tyr Gln Thr Ser Asp Asn Tyr Ser Gly His Val Gly Ala Leu Val Gly Val Ser Thr Pro
TAT CAA ACT TCT GAT AAC TAT TCT GGT CAC GTT GCA TTG GTA GGT GTG AGT ACG CCT 525                 530                 535                 540
Gln Glu Ala Thr Leu Pro Asn Ile Ile Gly Gln Pro Asp Glu Gln Gly Asn Val Ser Thr
CAA GAG GCT ACT CTT CCT AAT ATT ATA GGT CAA CCA GAT GAA CAG GGA AAT GTA TCT ACA 545                 550                 555                 560
Met Gly Phe Pro Phe Glu Lys Ala Ser Tyr Gly Gly Thr Val Val Lys Glu Trp Leu Asn
ATG GGA TTT CCG TTT GAA AAA GCT TCT TAT GGA GGT ACA GTT GTT AAA GAA TGG TTA AAT 565                 570                 575                 580
Gly Ala Asn Ala Met Lys Leu Ser Pro Gly Gln Ser Ile Gly Ile Pro Ile Thr Asn Val
GGT GCG AAT GCG ATG AAG CTT TCT CCT GGG CAA TCT ATA GGT ATT CCT ATT ACA AAT GTA 585                 590                 595                 600
Thr Ser Gly Glu Tyr Gln Ile Arg Cys Arg Tyr Ala Ser Asn Asp Asn Thr Asn Val Phe
ACA AGT GGA GAA TAT CAA ATT CGT TGT CGT TAT GCA AGT AAT GAT AAT ACT AAC GTT TTC
```

Figure 3E

```
                          605                      610                      615              620
Phe Asn Val Asp Thr Gly Gly Ala Asn Pro Ile Phe Gln Gln Ile Asn Phe Ala Ser Thr
TTT AAT GTA GAT ACT GGT GGA GCA AAT CCA ATT TTC CAA CAG ATA AAC TTT GCA TCT ACT 625                      630                      635              640
Val Asp Asn Asn Thr Gly Val Gln Gly Ala Asn Gly Val Tyr Val Val Lys Ser Ile Ala
GTA GAT AAT AAT ACG GGA GCA CAA GGA GTA CAA AAT GGT GTC TAT GTA AAA TCT ATT GCT 645                      650                      655              660
Thr Thr Asp Asn Ser Phe Thr Glu Ile Pro Ala Lys Thr Ile Asn Val His Leu Thr Asn
ACA ACT GAT AAT TCT TTT ACA GAA ATT CCT GCG AAG ACG ATT AAT GTT CAT TTA ACC AAC 665                      670                      675              680
Gln Gly Ser Ser Asp Val Phe Leu Asp Arg Ile Glu Phe Ile Pro Phe Ser Leu Pro Leu
CAA GGT TCT TCT GAT GTC TTT TTA GAC CGT ATT GAA TTT ATA CCT TTT TCT CTA CCT CTT 685                      690                      695              700
Ile Tyr His Gly Ser Tyr Asn Thr Ser Ser Gly Ala Asp Asp Val Leu Trp Ser Ser Ser
ATA TAT CAT GGA AGT TAT AAT ACT TCA GGT GCA GAT GAT GTT TTA TGG TCT TCT TCA
                                               705                      710                      715                      720
Asn Met Asn Tyr Tyr Asp Ile Ile Val Asn Gly Gln Ala Asn Ser Ser Ile Ala Ser
AAT ATG AAT TAC TAC GAT ATA ATA GTA AAT GGT CAG GCC AAT AGT AGT ATC GCT AGT
```

Figure 3F

```
                            725                   730                   735                   740
    Ser Met His Leu Leu Asn Lys Gly Lys Val Ile Lys Thr Ile Asp Ile Pro Gly His Ser
    TCT ATG CAT TTG CTT AAT AAA GGA AAA GTG ATA AAA ACA ATT GAT ATT CCA GGG CAT TCG
                            745                   750                   755                   760
    Glu Thr Phe Phe Ala Thr Phe Pro Val Pro Glu Gly Phe Asn Glu Val Arg Ile Leu Ala
    GAA ACC TTC TTT GCT ACG TTC CCA GTT CCA GAA GGA TTT AAT GAA GTT AGA ATT CTT GCT
                            765                   770                   775                   780
    Gly Leu Pro Glu Val Ser Gly Asn Ile Thr Val Gln Ser Asn Asn Pro Pro Gln Pro Ser
    GGC CTT CCA GAA GTT AGT GGA AAT ATT ACC GTA CAA TCT AAT AAT CCG CCT CAA CCT AGT
                            785                   790                   795                   800
    Asn Asn Gly Gly Asp Gly Gly Gly Gly Asn Gly Gly Asp Gly Gly Gln Tyr Asn Phe
    AAT AAT GGT GGT GAT GGT GGT GGT GGT AAT GGT GGT GAT GGT GGT CAA TAC AAT TTT
                            805                   810                   815                   820
    Ser Leu Ser Gly Ser Asp His Thr Thr Ile Tyr His Gly Lys Leu Glu Thr Gly Ile His
    TCT TTA AGC GGA TCT GAT CAT ACG ACT ATT TAT CAT GGA AAA CTT GAA ACT GGG ATT CAT
                            825                                     835                   840
    Val Gln Gly Asn Tyr Thr Tyr Thr Gly Thr Pro Val Leu Ile Leu Asn Ala Tyr Arg Asn
    GTA CAA GGT AAT TAT ACC TAT ACA GGT ACT CCC GTA TTA ATA CTG AAT GCT TAC AGA AAT
```

Figure 3G

```
                845                          850                          855                          860
Asn Thr Val Val Ser Ser Ile Pro Val Tyr Ser Pro Phe Asp Ile Thr Ile Gln Thr Glu
AAT ACT GTA GTA TCA AGC ATT CCA GTA TAT TCT CCT TTT GAT ATA ACT ATA CAG ACA GAA 865                          870                          875                          880
Ala Asp Ser Leu Glu Leu Gln Pro Arg Tyr Gly Phe Ala Thr Val Asn Gly Thr
GCT GAT AGC CTT GAG CTT GAA CTA CAA CCT AGA TAT GGT TTT GCC ACA GTG AAT GGT ACT 885                          890                          895                          900
Ala Thr Val Lys Ser Pro Asn Val Asn Tyr Asp Arg Ser Phe Lys Leu Pro Ile Asp Leu
GCA ACA GTA AAA AGT CCT AAT GTA AAT TAC GAT AGA TCA TTT AAA CTC CCA ATA GAC TTA 905                          910                          915                          920
Gln Asn Ile Thr Thr Gln Val Asn Ala Leu Phe Ala Ser Gly Thr Gln Asn Met Leu Ala
CAA AAT ATC ACA ACA CAA GTA AAT GCA TTA TTC GCA TCT GGA ACA CAA AAT ATG CTT GCT 925                          930                          935                          940
His Asn Val Ser Asp His Asp Ile Glu Gly Val Val Leu Lys Val Asp Ala Leu Ser Asp
CAT AAT GTA AGT GAT CAT GAT ATT GAA GGT GTA TTA AAA GTG GAT GCC TTA TCA GAT 945                          950                          955                          960
Glu Val Phe Gly Asp Glu Lys Lys Ala Leu Arg Lys Leu Val Asn Gln Ala Lys Arg Leu
GAA GTA TTT GGA GAT GAG AAG AAG GCT TTA CGT AAA TTG GTG AAT CAA GCA AAA CGT TTG
```

Figure 3H

```
              965                        970                        975                        980
Ser Arg Ala Arg Asn Leu Ile Gly Gly Ser Phe Glu Asn Trp Asp Ala Trp Tyr Lys
AGT AGA GCA AGA AAT CTT ATA GGT GGG AGT TTT GAA AAT TGG GAT GCA TGG TAT AAA 985                        990                        995                       1000
Gly Arg Asn Val Thr Val Ser Asp His Glu Leu Phe Lys Ser Asp His Val Leu Leu
GGA AGA AAT GTA ACT GTA TCT GAT CAT GAA CTA TTT AAG AGT GAT CAT GTA TTA TTA 1005                       1010                       1015                       1020
Pro Pro Gly Leu Ser Pro Ser Tyr Ile Phe Gln Lys Val Glu Glu Ser Lys Leu Lys
CCA CCA GGA TTG TCT CCA TCT TAT ATT TTC CAA AAA GTG GAG GAA TCT AAA TTA AAA 1025                       1030                       1035                       1040
Pro Asn Thr Arg Tyr Ile Val Ser Gly Phe Ile Ala His Gly Lys Asp Leu Glu Ile Val
CCA AAT ACA CGT TAT ATT GTT TCT GGA TTC ATC GCA CAT GGA AAA GAC CTA GAA ATT GTT 1045                       1050                       1055                       1060
Val Ser Arg Tyr Gly Gln Glu Val Gln Lys Val Val Gln Val Pro Tyr Gly Glu Ala Phe
GTT TCA CGT TAT GGG CAA GAA GTG CAA AAG GTC GTG CAA GTT CCT TAT GGA GAA GCA TTC 1065                       1070                       1075                       1080
Pro Leu Thr Ser Asn Gly Pro Val Cys Cys Pro Pro Arg Ser Thr Ser Asn Gly Thr Leu
CCG TTA ACA TCA AAT GGA CCA GTT TGT TGT CCC CCA CGT TCT ACA AGT AAT GGA ACC TTA
```

Figure 3I

```
                1085                    1090                    1095                    1100
Gly Asp Pro His Phe Phe Ser Tyr Ser Ile Asp Val Gly Ala Leu Asp Leu Gln Ala Asn
GGA GAT CCA CAT TTC TTC TTT AGT TAC AGT ATC GAT GTA GGT GCA CTA GAT TTA CAA GCA AAC
                           1105                    1110                    1115                    1120
Pro Gly Ile Glu Phe Gly Leu Arg Ile Val Asn Pro Thr Gly Met Ala Arg Val Ser Asn
CCT GGT ATT GAA TTT GGT CTT CGT ATT GTA AAT CCA ACT GGA ATG GCA CGC GTA AGC AAT
                1125                    1130                    1135                    1140
Leu Glu Ile Arg Glu Asp Arg Pro Leu Ala Ala Asn Glu Ile Arg Gln Val Gln Arg Val
TTG GAA ATT CGT GAA GAT CGT CCA TTA GCA GCA AAT GAA ATA CGA CAA GTA CAA CGT GTC
                1145                    1150                    1155                    1160
Ala Arg Asn Trp Arg Thr Glu Tyr Glu Lys Glu Arg Ala Glu Val Thr Ser Leu Ile Gln
GCA AGA AAT TGG AGA ACC GAG TAT GAG AAA GAA CGT GCG GAA GTA ACA AGT TTA ATT CAA
                1165                    1170                    1175                    1180
Pro Val Ile Asn Arg Ile Asn Gly Leu Tyr Glu Asn Gly Asn Trp Asn Gly Ser Ile Arg
CCT GTT ATC AAT CGA ATC AAC GGA TTG TAT GAA AAT GGA AAT TGG AAC GGT TCT ATT CGT
                1185                    1190                    1195                    1200
Ser Asp Ile Ser Tyr Gln Asn Ile Asp Ala Ile Val Leu Pro Thr Leu Pro Lys Leu Arg
TCA GAT ATT TCG TAT CAG AAT ATA GAC GCG ATT GTA TTA CCA ACG TTA CCA AAG TTA CGC
```

Figure 3J

```
                                                    1215                                      1220
His Trp Phe Met Ser Asp Arg Phe Ser Glu Gln Gly Asp Ile Met Ala Lys Phe Gln Gly
CAT TGG TTT ATG TCA GAT AGA TTC AGT GAA CAA GGA GAT ATA ATG GCT AAA TTC CAA GGT 1225                                  1235                                      1240
Ala Leu Asn Arg Ala Tyr Ala Gln Leu Gln Ser Thr Leu Leu His Asn Gly His Phe
GCA TTA AAT CGT GCG TAT GCA CAA CTG GAA CAA AGT ACG CTT CTG CAT AAT GGT CAT TTT 1245                                  1255                                      1260
Thr Lys Asp Ala Ala Asn Trp Thr Ile Glu Gly Asp Ala His Gln Ile Thr Leu Glu Asp
ACA AAA GAT GCA GCT AAT TGG ACA ATA GAA GGC GAT GCA CAT CAG ATA ACA CTA GAA GAT 1265                                  1275                                      1280
Gly Arg Arg Val Leu Arg Leu Pro Asp Trp Ser Ser Ser Val Ser Gln Met Ile Glu Ile
GGT AGA CGT GTA TTG CGA CTT CCA GAT TGG TCT TCG AGT GTA TCT CAA ATG ATT GAA ATC 1285                                  1295                                      1300
Glu Asn Phe Asn Pro Asp Lys Glu Tyr Asn Leu Val Phe His Gly Gln Gly Glu Gly Thr
GAG AAT TTT AAT CCA GAT AAA GAA TAC AAC TTA GTA TTC CAT GGG CAA GGA GAA GGA ACG 1305                                  1315                                      1320
Val Thr Leu Glu His Gly Glu Glu Thr Lys Tyr Ile Glu Thr His His His Thr His Phe Ala
GTT ACG TTG GAG CAT GGA GAG GAA ACA AAA TAT ATA GAA ACG CAT CAT ACA CAT TTT GCG
```

Figure 3K

```
                            1325                            1330                            1335                            1340
Asn Phe Thr Thr Ser Gln Arg Gln Gly Leu Thr Phe Glu Ser Asn Lys Val Thr Val Thr
AAT TTT ACA ACT TCT CAA CGT CAA GGA CTC ACG TTT GAA TCA AAT AAA GTG ACA GTG ACC 1345                            1350                            1355                            1360
Ile Ser Ser Glu Asp Gly Glu Phe Leu Val Asp Asn Ile Ala Leu Val Glu Ala Pro Leu
ATT TCT TCA GAA GAT GGA GAA TTC TTA GTG GAT AAT ATT GCG CTT GTG GAA GCT CCT CTT 1365                            1370                            1375                            1380
Pro Thr Asp Asp Gln Asn Ser Glu Gly Asn Thr Ala Ser Ser Thr Asn Ser Asp Thr Ser
CCT ACA GAT GAC CAA AAT TCT GAG GGA AAT ACG GCT TCC AGT ACG AAT AGC GAT ACA AGT

1385
Met Asn Asn Asn Gln Gln
ATG AAC AAC AAT CAA
```

Figure 3L

```
   1  ATGGCAATTT TAAATGAATT ATATCCATCT GTACCTTATA ATGTATTGGC
  51  GTATACGCCA CCCTCTTTTT TACCTGATGC GGGTACACAA GCTACACCTG
 101  CTGACTTAAC AGCTTATGAA CAATTGTTGA AAAATTTAGA AAAAGGGATA
 151  AATGCTGGAA CTTATTCGAA AGCAATAGCT GATGTACTTA AAGGTATTTT
 201  TATAGATGAT ACAATAAATT ATCAAACATA TGTAAATATT GGTTTAAGTT
 251  TAATTACATT AGCTGTACCG GAAATTGGTA TTTTACACC TTTCATCGGT
 301  TTGTTTTTTG CTGCATTGAA TAAACATGAT GCTCCACCTC CTCCTAATGC
 351  AAAAGATATA TTTGAGGCTA TGAAACCAGC GATTCAAGAG ATGATTGATA
 401  GAACTTTAAC TGCGGATGAG CAAACATTTT TAAATGGGGA ATAAGTGGT
 451  TTACAAAATT TAGCAGCAAG ATACCAGTCT ACAATGGATG ATATTCAAAG
 501  CCATGGAGGA TTTAATAAGG TAGATTCTGG ATTAATTAAA AAGTTTACAG
 551  ATGAGGTACT ATCTTTAAAT AGTTTTTATA CAGATCGTTT ACCTGTATTT
 601  ATTACAGATA ATACAGCGGA TCGAACTTTG TTAGGTCTTC CTTATTATGC
 651  TATACTTGCG AGCATGCATC TTATGTTATT AAGAGATATC ATTACTAAGG
 701  GTCCGACATG GGATTCTAAA ATTAATTTCA CACCAGATGC AATTGATTCC
 751  TTTAAAACCG ATATTAAAAA TAATATAAAG CTTTACTCTA AAACTATTTA
 801  TGACGTATTT CAGAAGGGAC TTGCTTCATA CGGAACGCCT TCTGATTTAG
 851  AGTCCTTTGC AAAAAAACAA AAATATATTG AAATTATGAC AACACATTGT
 901  TTAGATTTTG CAAGATTGTT TCCTACTTTT GATCCAGATC TTTATCCAAC
 951  AGGATCAGGT GATATAAGTT TACAAAAAAC ACGTAGAATT CTTTCTCCTT
1001  TTATCCCTAT ACGTACTGCA GATGGGTTAA CATTAAATAA TACTTCAATT
1051  GATACTTCAA ATTGGCCTAA TTATGAAAAT GGGAATGGCG CGTTTCCAAA
1101  CCCAAAAGAA AGAATATTAA ACAATTCAA ACTGTATCCT AGTTGGAGAG
1151  CGGGACAGTA CGGTGGGCTT TTACAACCTT ATTTATGGGC AATAGAAGTC
1201  CAAGATTCTG TAGAGACTCG TTTGTATGGG CAGCTTCCAG CTGTAGATCC
1251  ACAGGCAGGG CCTAATTATG TTTCCATAGA TTCTTCTAAT CCAATCATAC
1301  AAATAAATAT GGATACTTGG AAAACACCAC CACAAGGTGC GAGTGGGTGG
1351  AATACAAATT TAATGAGAGG AAGTGTAAGC GGGTTAAGTT TTTTACAACG
```

Figure 4A

```
1401  AGATGGTACG AGACTTAGTG CTGGTATGGG TGGTGGTTTT GCTGATACAA

1451  TATATAGTCT CCCTGCAACT CATTATCTTT CTTATCTCTA TGGAACTCCT

1501  TATCAAACTT CTGATAACTA TTCTGGTCAC GTTGGTGCAT TGGTAGGTGT

1551  GAGTACGCCT CAAGAGGCTA CTCTTCCTAA TATTATAGGT CAACCAGATG

1601  AACAGGGAAA TGTATCTACA ATGGGATTTC CGTTTGAAAA AGCTTCTTAT

1651  GGAGGTACAG TTGTTAAAGA ATGGTTAAAT GGTGCGAATG CGATGAAGCT

1701  TTCTCCTGGG CAATCTATAG GTATTCCTAT TACAAATGTA ACAAGTGGAG

1751  AATATCAAAT TCGTTGTCGT TATGCAAGTA ATGATAATAC TAACGTTTTC

1801  TTTAATGTAG ATACTGGTGG AGCAAATCCA ATTTTCCAAC AGATAAACTT

1851  TGCATCTACT GTAGATAATA ATACGGGAGT ACAAGGAGCA AATGGTGTCT

1901  ATGTAGTCAA ATCTATTGCT ACAACTGATA ATTCTTTTAC AGTAAAAATT

1951  CCTGCGAAGA CGATTAATGT TCATTTAACC AACCAAGGTT CTTCTGATGT

2001  CTTTTTAGAT CGTATTGAGT TTGTTCCAAT TCTAGAATCA AATACTGTAA

2051  CTATATTCAA CAATTCATAT ACTACAGGTT CAGCAAATCT TATACCAGCA

2101  ATAGCTCCTC TTTGGAGTAC TAGTTCAGAT AAAGCCCTTA CAGGTTCTAT

2151  GTCAATAACA GGTCGAACTA CCCCTAACAG TGATGATGCT TTGCTTCGAT

2201  TTTTTAAAAC TAATTATGAT ACACAAACCA TTCCTATTCC GGGTTCCGGA

2251  AAAGATTTTA CAAATACTCT AGAAATACAA GACATAGTTT CTATTGATAT

2301  TTTTGTCGGA TCTGGTCTAC ATGGATCCGA TGGATCTATA AAATTAGATT

2351  TTACCAATAA TAATAGTGGT AGTGGTGGCT CTCCAAAGAG TTTCACCGAG

2401  CAAAATGATT TAGAGAATAT CACAACACAA GTGAATGCTC TATTCACATC

2451  TAATACACAA GATGCACTTG CAACAGATGT GAGTGATCAT GATATTGAAG

2501  AAGTGGTTCT AAAAGTAGAT GCATTATCTG ATGAAGTGTT TGGAAAAGAG

2551  AAAAAAACAT TGCGTAAATT TGTAAATCAA GCGAAGCGCT TAAGCAAGGC

2601  GCGTAATCTC CTGGTAGGAG GCAATTTTGA TAACTTGGAT GCTTGGTATA

2651  GAGGAAGAAA TGTAGTAAAC GTATCTAATC ACGAACTGTT GAAGAGTGAT

2701  CATGTATTAT TACCACCACC AGGATTGTCT CCATCTTATA TTTTCCAAAA

2751  AGTGGAGGAA TCTAAATTAA AACGAAATAC ACGTTATACG GTTTCTGGAT

2801  TTATTGCGCA TGCAACAGAT TTAGAAATTG TGGTTTCTCG TTATGGGCAA
```

Figure 4B

```
2851  GAAATAAAGA AAGTGGTGCA AGTTCCTTAT GGAGAAGCAT TCCCATTAAC
2901  ATCAAGTGGA CCAGTTTGTT GTATCCCACA TTCTACAAGT AATGGAACTT
2951  TAGGCAATCC ACATTTCTTT AGTTACAGTA TTGATGTAGG TGCATTAGAT
3001  GTAGACACAA ACCCTGGTAT TGAATTCGGT CTTCGTATTG TAAATCCAAC
3051  TGGAATGGCA CGCGTAAGCA ATTTGGAAAT TCGTGAAGAT CGTCCATTAG
3101  CAGCAAATGA AATACGACAA GTACAACGTG TCGCAAGAAA TTGGAGAACC
3151  GAGTATGAGA AGAACGTGC GGAAGTAACA AGTTTAATTC AACCTGTTAT
3201  CAATCGAATC AATGGATTGT ATGACAATGG AAATTGGAAC GGTTCTATTC
3251  GTTCAGATAT TTCGTATCAG AATATAGACG CGATTGTATT ACCAACGTTA
3301  CCAAAGTTAC GCCATTGGTT TATGTCAGAT AGATTTAGTG AACAAGGAGA
3351  TATCATGGCT AAATTCCAAG GTGCATTAAA TCGTGCGTAT GCACAACTGG
3401  AACAAAATAC GCTTCTGCAT AATGGTCATT TTACAAAAGA TGCAGCCAAT
3451  TGGACGGTAG AAGGCGATGC ACATCAGGTA GTATTAGAAG ATGGTAAACG
3501  TGTATTACGA TTGCCAGATT GGTCTTCGAG TGTGTCTCAA ACGATTGAAA
3551  TCGAGAATTT TGATCCAGAT AAAGAATATC AATTAGTATT TCATGGGCAA
3601  GGAGAAGGAA CGGTTACGTT GGAGCATGGA GAAGAAACAA AATATATAGA
3651  AACGCATACA CATCATTTTG CGAATTTTAC AACTTCTCAA CGTCAAGGAC
3701  TCACGTTTGA ATCAAATAAA GTGACAGTGA CCATTCTTC AGAAGATGGA
3751  GAATTCTTAG TGGATAATAT TGCGCTTGTA GAAGCTCCTC TTCCTACAGA
3801  TGACCAAAAT TCTGAGGGAA ATACGGCTTC CAGTACGAAT AGCGATACAA
3851  GTATGAACAA CAATCAA*
```

Figure 4C

```
                           5                          10                         15
  1 Met Ala Ile Leu Asn Glu Leu Tyr Pro Ser Val Pro Tyr Asn Val
 16 Leu Ala Tyr Thr Pro Pro Ser Phe Leu Pro Asp Ala Gly Thr Gln
 31 Ala Thr Pro Ala Asp Leu Thr Ala Tyr Glu Gln Leu Leu Lys Asn
 46 Leu Glu Lys Gly Ile Asn Ala Gly Thr Tyr Ser Lys Ala Ile Ala
 61 Asp Val Leu Lys Gly Ile Phe Ile Asp Asp Thr Ile Asn Tyr Gln
 76 Thr Tyr Val Asn Ile Gly Leu Ser Leu Ile Thr Leu Ala Val Pro
 91 Glu Ile Gly Ile Phe Thr Pro Phe Ile Gly Leu Phe Phe Ala Ala
106 Leu Asn Lys His Asp Ala Pro Pro Pro Pro Asn Ala Lys Asp Ile
121 Phe Glu Ala Met Lys Pro Ala Ile Gln Glu Met Ile Asp Arg Thr
136 Leu Thr Ala Asp Glu Gln Thr Phe Leu Asn Gly Glu Ile Ser Gly
151 Leu Gln Asn Leu Ala Ala Arg Tyr Gln Ser Thr Met Asp Asp Ile
166 Gln Ser His Gly Gly Phe Asn Lys Val Asp Ser Gly Leu Ile Lys
181 Lys Phe Thr Asp Glu Val Leu Ser Leu Asn Ser Phe Tyr Thr Asp
196 Arg Leu Pro Val Phe Ile Thr Asp Asn Thr Ala Asp Arg Thr Leu
211 Leu Gly Leu Pro Tyr Tyr Ala Ile Leu Ala Ser Met His Leu Met
226 Leu Leu Arg Asp Ile Ile Thr Lys Gly Pro Thr Trp Asp Ser Lys
241 Ile Asn Phe Thr Pro Asp Ala Ile Asp Ser Phe Lys Thr Asp Ile
256 Lys Asn Asn Ile Lys Leu Tyr Ser Lys Thr Ile Tyr Asp Val Phe
271 Gln Lys Gly Leu Ala Ser Tyr Gly Thr Pro Ser Asp Leu Glu Ser
286 Phe Ala Lys Lys Gln Lys Tyr Ile Glu Ile Met Thr Thr His Cys
301 Leu Asp Phe Ala Arg Leu Phe Pro Thr Phe Asp Pro Asp Leu Tyr
316 Pro Thr Gly Ser Gly Asp Ile Ser Leu Gln Lys Thr Arg Arg Ile
331 Leu Ser Pro Phe Ile Pro Ile Arg Thr Ala Asp Gly Leu Thr Leu
346 Asn Asn Thr Ser Ile Asp Thr Ser Asn Trp Pro Asn Tyr Glu Asn
361 Gly Asn Gly Ala Phe Pro Asn Pro Lys Glu Arg Ile Leu Lys Gln
376 Phe Lys Leu Tyr Pro Ser Trp Arg Ala Gly Gln Tyr Gly Gly Leu
391 Leu Gln Pro Tyr Leu Trp Ala Ile Glu Val Gln Asp Ser Val Glu
406 Thr Arg Leu Tyr Gly Gln Leu Pro Ala Val Asp Pro Gln Ala Gly
421 Pro Asn Tyr Val Ser Ile Asp Ser Ser Asn Pro Ile Ile Gln Ile
436 Asn Met Asp Thr Trp Lys Thr Pro Pro Gln Gly Ala Ser Gly Trp
451 Asn Thr Asn Leu Met Arg Gly Ser Val Ser Gly Leu Ser Phe Leu
466 Gln Arg Asp Gly Thr Arg Leu Ser Ala Gly Met Gly Gly Gly Phe
481 Ala Asp Thr Ile Tyr Ser Leu Pro Ala Thr His Tyr Leu Ser Tyr
496 Leu Tyr Gly Thr Pro Tyr Gln Thr Ser Asp Asn Tyr Ser Gly His
511 Val Gly Ala Leu Val Gly Val Ser Thr Pro Gln Glu Ala Thr Leu
526 Pro Asn Ile Ile Gly Gln Pro Asp Glu Gln Gly Asn Val Ser Thr
541 Met Gly Phe Pro Phe Glu Lys Ala Ser Tyr Gly Gly Thr Val Val
556 Lys Glu Trp Leu Asn Gly Ala Asn Ala Met Lys Leu Ser Pro Gly
571 Gln Ser Ile Gly Ile Pro Ile Thr Asn Val Thr Ser Gly Glu Tyr
586 Gln Ile Arg Cys Arg Tyr Ala Ser Asn Asp Asn Thr Asn Val Phe
601 Phe Asn Val Asp Thr Gly Gly Ala Asn Pro Ile Phe Gln Gln Ile
616 Asn Phe Ala Ser Thr Val Asp Asn Asn Thr Gly Val Gln Gly Ala
631 Asn Gly Val Tyr Val Val Lys Ser Ile Ala Thr Thr Asp Asn Ser
646 Phe Thr Val Lys Ile Pro Ala Lys Thr Ile Asn Val His Leu Thr
661 Asn Gln Gly Ser Ser Asp Val Phe Leu Asp Arg Ile Glu Phe Val
676 Pro Ile Leu Glu Ser Asn Thr Val Thr Ile Phe Asn Asn Ser Tyr
691 Thr Thr Gly Ser Ala Asn Leu Ile Pro Ala Ile Ala Pro Leu Trp
706 Ser Thr Ser Ser Asp Lys Ala Leu Thr Gly Ser Met Ser Ile Thr
721 Gly Arg Thr Thr Pro Asn Ser Asp Asp Ala Leu Leu Arg Phe Phe
736 Lys Thr Asn Tyr Asp Thr Gln Thr Ile Pro Ile Pro Gly Ser Gly
751 Lys Asp Phe Thr Asn Thr Leu Glu Ile Gln Asp Ile Val Ser Ile
766 Asp Ile Phe Val Gly Ser Gly Leu His Gly Ser Asp Gly Ser Ile
781 Lys Leu Asp Phe Thr Asn Asn Asn Ser Gly Ser Gly Gly Ser Pro
```

Figure 5A

```
 796 Lys Ser Phe Thr Glu Gln Asn Asp Leu Glu Asn Ile Thr Thr Gln
 811 Val Asn Ala Leu Phe Thr Ser Asn Thr Gln Asp Ala Leu Ala Thr
 826 Asp Val Ser Asp His Asp Ile Glu Glu Val Val Leu Lys Val Asp
 841 Ala Leu Ser Asp Glu Val Phe Gly Lys Glu Lys Lys Thr Leu Arg
 856 Lys Phe Val Asn Gln Ala Lys Arg Leu Ser Lys Ala Arg Asn Leu
 871 Leu Val Gly Gly Asn Phe Asp Asn Leu Asp Ala Trp Tyr Arg Gly
 886 Arg Asn Val Val Asn Val Ser Asn His Glu Leu Leu Lys Ser Asp
 901 His Val Leu Leu Pro Pro Pro Gly Leu Ser Pro Ser Tyr Ile Phe
 916 Gln Lys Val Glu Glu Ser Lys Leu Lys Arg Asn Thr Arg Tyr Thr
 931 Val Ser Gly Phe Ile Ala His Ala Thr Asp Leu Glu Ile Val Val
 946 Ser Arg Tyr Gly Gln Glu Ile Lys Lys Val Val Gln Val Pro Tyr
 961 Gly Glu Ala Phe Pro Leu Thr Ser Ser Gly Pro Val Cys Cys Ile
 976 Pro His Ser Thr Ser Asn Gly Thr Leu Gly Asn Pro His Phe Phe
 991 Ser Tyr Ser Ile Asp Val Gly Ala Leu Asp Val Asp Thr Asn Pro
1006 Gly Ile Glu Phe Gly Leu Arg Ile Val Asn Pro Thr Gly Met Ala
1021 Arg Val Ser Asn Leu Glu Ile Arg Glu Asp Arg Pro Leu Ala Ala
1036 Asn Glu Ile Arg Gln Val Gln Arg Val Ala Arg Asn Trp Arg Thr
1051 Glu Tyr Glu Lys Glu Arg Ala Glu Val Thr Ser Leu Ile Gln Pro
1066 Val Ile Asn Arg Ile Asn Gly Leu Tyr Asp Asn Gly Asn Trp Asn
1081 Gly Ser Ile Arg Ser Asp Ile Ser Tyr Gln Asn Ile Asp Ala Ile
1096 Val Leu Pro Thr Leu Pro Lys Leu Arg His Trp Phe Met Ser Asp
1111 Arg Phe Ser Glu Gln Gly Asp Ile Met Ala Lys Phe Gln Gly Ala
1126 Leu Asn Arg Ala Tyr Ala Gln Leu Glu Gln Asn Thr Leu Leu His
1141 Asn Gly His Phe Thr Lys Asp Ala Ala Asn Trp Thr Val Glu Gly
1156 Asp Ala His Gln Val Val Leu Glu Asp Gly Lys Arg Val Leu Arg
1171 Leu Pro Asp Trp Ser Ser Ser Val Ser Gln Thr Ile Glu Ile Glu
1186 Asn Phe Asp Pro Asp Lys Glu Tyr Gln Leu Val Phe His Gly Gln
1201 Gly Glu Gly Thr Val Thr Leu Glu His Gly Glu Glu Thr Lys Tyr
1216 Ile Glu Thr His Thr His His Phe Ala Asn Phe Thr Thr Ser Gln
1231 Arg Gln Gly Leu Thr Phe Glu Ser Asn Lys Val Thr Val Thr Ile
1246 Ser Ser Glu Asp Gly Glu Phe Leu Val Asp Asn Ile Ala Leu Val
1261 Glu Ala Pro Leu Pro Thr Asp Asp Gln Asn Ser Glu Gly Asn Thr
1276 Ala Ser Ser Thr Asn Ser Asp Thr Ser Met Asn Asn Asn Gln
```

Fragment 1-*

Figure 5B

```
Met Ala Ile Leu Asn  Glu Leu Tyr Pro Ser  Val Pro Tyr Asn Val  Leu Ala Tyr Thr Pro
ATG GCA ATT TTA AAT  GAA TTA TAT CCA TCT  GTA CCT TAT AAT GTA  TTG GCG TAT ACG CCA
                 5                    10                   15                   20

Pro Ser Phe Leu Pro  Asp Ala Gly Thr Gln  Ala Thr Pro Ala Asp  Leu Thr Ala Tyr Glu
CCC TCT TTT TTA CCT  GAT GCG GGT ACA CAA  GCT ACA CCT GCT GAC  TTA ACA GCT TAT GAA
                25                    30                   35                   40

Gln Leu Lys Asn Leu  Glu Lys Gly Ile Asn  Ala Gly Thr Tyr Ser  Lys Ala Ile Ala
CAA TTG AAA AAT TTA  GAA AAA GGG ATA AAT  GCT GGA ACT TAT TCG  AAA GCA ATA GCT
                45                    50                   55                   60

Asp Val Leu Gly Ile  Phe Ile Asp Thr Ile  Asn Tyr Gln Thr Tyr  Val Asn Ile Ile
GAT GTA CTT GGT ATT  TTT ATA GAT ACA ATA  AAT TAT CAA ACA TAT  GTA AAT ATA ATT
                65                    70                   75                   80

Gly Leu Ser Leu Ile  Thr Leu Ile Thr Leu  Ala Val Pro Glu Ile  Phe Thr Pro Phe Ile Gly
GGT TTA AGT TTA ATT  ACA TTA ATT ACA TTA  GCT GTA CCG GAA ATT  TTT ACA CCT TTC ATC GGT
                85                    90                   95                  100

Leu Phe Phe Ala Ala  Leu Asn Lys His Asp  Ala Pro Pro Asn Ala  Lys Asp Ile
TTG TTT TTT GCT GCA  TTG AAT AAA CAT GAT  GCT CCA CCT AAT GCA  AAA GAT ATA
               105                   110                  115                  120
```

Figure 6A

```
Phe Glu Ala Met Lys Pro Ala Ile Gln Met Ile Asp Arg Thr Leu Thr Ala Asp Glu
TTT GAG GCT ATG AAA CCA GCG ATT CAA GAG ATG ATT GAT AGA ACT TTA ACT GCG GAT GAG
                    125                 130                 135                 140

Gln Thr Phe Leu Asn Gly Glu Ile Ser Gly Leu Gln Asn Leu Ala Ala Arg Tyr Gln Ser
CAA ACA TTT TTA AAT GGG GAA ATA AGT GGT TTA CAA AAT TTA GCA GCA AGA TAC CAG TCT
                    145                 150                 155                 160

Thr Met Asp Asp Ile Gln Ser His Gly Phe Asn Lys Val Asp Ser Gly Leu Ile Lys
ACA ATG GAT GAT ATT CAA AGC CAT GGA TTT AAT AAG GTA GAT TCT GGA TTA ATT AAA
                    165                 170                 175                 180

Lys Phe Thr Asp Glu Val Leu Ser Leu Asn Ser Phe Tyr Thr Asp Arg Leu Pro Val Phe
AAG TTT ACA GAT GAG GTA CTA TCT TTA AAT AGT TTT TAT ACA GAT CGT TTA CCT GTA TTT
                    185                 190                 195                 200

Ile Asp Asn Thr Ala Asp Arg Thr Arg Thr Leu Leu Gly Leu Pro Tyr Tyr Ala Ile Leu Ala
ATT GAT AAT GCG GAT CGA ACT CTT TTA GGT CTT CCT TAT TAT GCT ATA CTT GCG
                    205                 210                 215                 220

Ser His Leu Met Leu Arg Asp Ile Ile Thr Lys Gly Pro Thr Trp Asp Ser Lys
AGC CAT CTT ATG TTA TTA AGA GAT ATC ATT ACT AAG GGT CCG ACA TGG GAT TCT AAA
                    225                 230                 235                 240

Ser Met His Leu Met Leu Arg Asp Ile Ile Thr Lys Gly Pro Thr Trp Asp Ser Lys
AGC CAT CTT ATG TTA TTA AGA GAT ATC ATT ACT AAG GGT CCG ACA TGG GAT TCT AAA
                    225                 230                 235                 240

Ile Asn Phe Thr Pro Asp Ala Ile Ile Asp Ser Phe Lys Thr Asp Ile Lys Asn Asn Ile Lys
ATT AAT TTC ACA CCA GAT GCA ATT GAT TCC TTT AAA ACC GAT ATT AAA AAT AAT ATA AAG
                    245                 250                 255                 260
```

Figure 6B

```
Leu Tyr Ser Lys Thr Ile Tyr Asp Val Phe Gln Lys Gly Leu Ala Ser Tyr Gly Thr Pro
CTT TAC TCT AAA ACT ATT TAT GAC GTA TTT CAG AAG GGA CTT GCT TCA TAC GGA ACG CCT
            265             270             275             280

Ser Asp Leu Glu Ser Phe Ala Lys Lys Tyr Gln Lys Tyr Ile Glu Ile Met Thr Thr His Cys
TCT GAT TTA GAG TCC TTT GCA AAA AAA TAT CAA AAA TAT ATT GAA ATT ATG ACA ACA CAT TGT
            285             290             295             300

Leu Asp Phe Ala Arg Leu Phe Pro Thr Phe Asp Pro Asp Leu Tyr Pro Thr Gly Ser Gly
TTA GAT TTT GCA AGA TTG TTT CCT ACT TTT GAT CCA GAT CTT TAT CCA ACA GGA TCA GGT
            305             310             315             320

Asp Ile Ser Leu Gln Lys Lys Thr Arg Arg Ile Leu Ser Pro Phe Ile Pro Ile Arg Thr Ala
GAT ATA AGT TTA CAA AAA ACA CGT AGA ATT CTT TCT CCT TTT ATC CCT ATA CGT ACT GCA
            325             330             335             340

Asp Gly Leu Thr Leu Asn Asn Thr Ile Asp Thr Ser Asn Trp Pro Asn Tyr Glu Asn
GAT GGG TTA ACA TTA AAT AAT ACT TCA ATT GAT ACT TCA AAT TGG CCT AAT TAT GAA AAT
            345             350             355             360

Gly Asn Gly Ala Phe Pro Asn Pro Lys Glu Arg Ile Leu Lys Gln Phe Lys Leu Tyr Pro
GGG AAT GGC GCG TTT CCA AAC CCA AAA GAA AGA ATA TTA AAA CAA TTC AAA CTG TAT CCT
            365             370             375             380

Ser Trp Arg Ala Gly Gln Tyr Gly Gly Leu Leu Gln Pro Tyr Leu Trp Ala Ile Glu Val
AGT TGG AGA GCG GGA CAG TAC GGT GGG CTT TTA CAA CCT TAT TTA TGG GCA ATA GAA GTC
            385             390             395             400
```

Figure 6C

```
                    405                415                    420
Gln Asp Ser Val Glu Thr Arg Leu Tyr Gly Gln Leu Pro Ala Val Asp Pro Gln Ala Gly
CAA GAT TCT GTA GAG ACT CGT TTG TAT GGG CAG CTT CCA GCT GTA GAT CCA CAG GCA GGG 425                435                    440
Pro Asn Tyr Val Ser Ile Asp Ser Ser Asn Pro Ile Ile Gln Ile Asn Met Asp Thr Trp
CCT AAT TAT GTT TCC ATA GAT TCT AAT CCA ATC ATA CAA ATA AAT ATG GAT ACT TGG 445                455                    460
Lys Thr Pro Pro Gln Gly Ala Ser Gly Trp Asn Thr Asn Leu Met Arg Gly Ser Val Ser
AAA ACA CCA CCA CAA GGT GCG AGT GGG TGG AAT ACA AAT TTA ATG AGA GGA AGT GTA AGC 465                475                    480
Gly Leu Ser Phe Leu Gln Arg Asp Gly Thr Arg Leu Ser Ala Gly Met Gly Gly Phe
GGG TTA AGT TTT TTA CAA CGA GAT GGT ACG AGA CTT AGT GCT GGT ATG GGT GGT TTT 485                495                    500
Ala Asp Thr Ile Tyr Ser Leu Pro Ala Thr His Tyr Leu Ser Tyr Gly Thr Pro
GCT GAT ACA ATA TAT AGT CTC CCT GCA ACT CAT TAT CTT TCT TAT GGA ACT CCT 505                515                    520
Tyr Gln Thr Ser Asp Asn Tyr Ser Gly His Val Gly Val Leu Val Ser Thr Pro
TAT CAA ACT TCT GAT AAC TAT TCT GGT CAC GTT GGT GCA TTG GTA AGT ACG CCT 525                535                    540
Gln Glu Ala Thr Leu Pro Asn Ile Ile Gly Gln Pro Asp Glu Gln Gly Asn Val Ser Thr
CAA GAG GCT ACT CTT CCT AAT ATT ATA GGT CAA CCA GAT GAA CAG GGA AAT GTA TCT ACA
```

Figure 6D

```
                545             550             555             560
Met Gly Phe Pro Glu Lys Ala Ser Tyr Gly Gly Thr Val Val Lys Glu Trp Leu Asn
ATG GGA TTT CCG GAA AAA GCT TCT TAT GGA GGT ACA GTT AAA GAA TGG TTA AAT 565             570             575             580
Gly Ala Asn Ala Met Lys Leu Ser Pro Gly Gln Ser Ile Gly Ile Pro Ile Thr Asn Val
GGT GCG AAT GCG ATG AAG CTT TCT CCT GGG CAA TCT ATA GGT ATT CCT ATT ACA AAT GTA 585             590             595             600
Thr Ser Gly Glu Gln Tyr Gln Ile Arg Cys Arg Tyr Ala Ser Asn Asp Asn Thr Asn Val Phe
ACA AGT GGA GAA CAA TAT CAA ATT CGT TGT CGT TAT GCA AGT AAT GAT AAT ACT AAC GTT TTC 605             610             615             620
Phe Asn Val Asp Thr Gly Gly Ala Asn Pro Ile Phe Gln Gln Ile Asn Phe Ala Ser Thr
TTT AAT GTA GAT ACT GGT GGA GCA AAT CCA ATT TTC CAA CAG ATA AAC TTT GCA TCT ACT 625             630             635             640
Val Asp Asn Asn Thr Gly Val Gln Gly Ala Asn Gly Val Tyr Val Val Lys Ser Ile Ala
GTA GAT AAT AAT ACG GGA GTA CAA GGA GCA AAT GGT GTC TAT GTA GTC AAA TCT ATT GCT 645             650             655             660
Thr Thr Asp Asn Ser Phe Thr Val Lys Ile Pro Ala Lys Thr Ile Asn Val His Leu Thr
ACA ACT GAT AAT TCT TTT ACA GTA AAA ATT CCT GCG AAG ACG ATT AAT GTT CAT TTA ACC 665             670             675             680
Asn Gln Gly Ser Ser Asp Val Phe Leu Asp Arg Ile Glu Phe Val Pro Ile Leu Glu Ser
AAC CAA GGT TCT TCT GAT GTC TTT TTA GAT CGT ATT GAG TTT GTT CCA ATT CTA GAA TCA
```

Figure 6E

| Pos | 685 | | | | 690 | | | | 695 | | | | 700 |
|---|---|---|---|---|---|---|---|---|---|---|---|---|---|
| | Asn | Thr | Val | Thr | Ile | Phe | Asn | Asn | Ser | Tyr | Thr | Thr | Gly | Ser | Ala | Asn | Leu | Ile | Pro | Ala |
| | AAT | ACT | GTA | ACT | ATA | TTC | AAC | AAT | TCA | TAT | ACT | ACA | GGT | TCA | GCA | AAT | CTT | ATA | CCA | GCA |

| Pos | 705 | | | | 710 | | | | 715 | | | | 720 |
|---|---|---|---|---|---|---|---|---|---|---|---|---|---|
| | Ile | Ala | Pro | Leu | Trp | Ser | Thr | Ser | Ser | Asp | Lys | Ala | Leu | Thr | Gly | Ser | Met | Ser | Ile | Thr |
| | ATA | GCT | CCT | CTT | TGG | AGT | ACT | AGT | TCA | GAT | AAA | GCC | CTT | ACA | GGT | TCT | ATG | TCA | ATA | ACA |

| Pos | 725 | | | | 730 | | | | 735 | | | | 740 |
|---|---|---|---|---|---|---|---|---|---|---|---|---|---|
| | Gly | Arg | Thr | Thr | Pro | Asn | Ser | Asp | Asp | Ala | Leu | Leu | Arg | Phe | Lys | Thr | Asn | Tyr | Asp |
| | GGT | CGA | ACT | ACC | CCT | AAC | AGT | GAT | GAT | GCT | TTG | CTT | CGA | TTT | AAA | ACT | AAT | TAT | GAT |

| Pos | 745 | | | | 750 | | | | 755 | | | | 760 |
|---|---|---|---|---|---|---|---|---|---|---|---|---|---|
| | Thr | Gln | Thr | Ile | Pro | Ile | Pro | Gly | Ser | Gly | Lys | Asp | Phe | Thr | Phe | Asn | Thr | Leu | Glu | Ile | Gln |
| | ACA | CAA | ACC | ATT | CCT | ATT | CCG | GGT | TCC | GGA | AAA | GAT | TTT | ACA | AAT | ACT | CTA | GAA | ATA | CAA |

| Pos | 765 | | | | 770 | | | | 775 | | | | 780 |
|---|---|---|---|---|---|---|---|---|---|---|---|---|---|
| | Asp | Ile | Val | Ser | Ile | Phe | Val | Gly | Ser | Gly | Leu | His | Gly | Ser | Asp | Gly | Ser | Ile |
| | GAC | ATA | GTT | TCT | ATT | GAT | ATT | TTT | GTC | GGA | TCT | CTA | CAT | GGA | TCC | GAT | GGA | TCT | ATA |

| Pos | 785 | | | | 790 | | | | 795 | | | | 800 |
|---|---|---|---|---|---|---|---|---|---|---|---|---|---|
| | Lys | Leu | Asp | Phe | Thr | Asn | Asn | Asn | Ser | Gly | Ser | Gly | Gly | Ser | Pro | Lys | Ser | Phe | Thr | Glu |
| | AAA | TTA | GAT | TTT | ACC | AAT | AAT | AAT | AGT | GGT | AGT | GGT | GGC | TCT | CCA | AAG | AGT | TTC | ACC | GAG |

| Pos | 805 | | | | 810 | | | | 815 | | | | 820 |
|---|---|---|---|---|---|---|---|---|---|---|---|---|---|
| | Gln | Asn | Asp | Leu | Glu | Asn | Ile | Thr | Thr | Gln | Val | Asn | Ala | Leu | Phe | Thr | Ser | Asn | Thr | Gln |
| | CAA | AAT | GAT | TTA | GAG | AAT | ATC | ACA | ACA | CAA | GTG | AAT | GCT | CTA | TTC | ACA | TCT | AAT | ACA | CAA |

Figure 6F

```
                            825                 830                 835                 840
Asp Ala Leu Ala Thr Asp Val Ser Asp His Asp Ile Glu Glu Val Val Leu Lys Val Asp
GAT GCA CTT GCA ACA GAT GTG AGT GAT CAT GAT ATT GAA GAA GTG GTT CTA AAA GTA GAT 845                 850                 855                 860
Ala Leu Ser Asp Glu Val Phe Gly Lys Glu Lys Thr Leu Arg Lys Phe Val Asn Gln
GCA TTA TCT GAT GAA GTG TTT GGA AAA GAG AAA ACA TTG CGT AAA TTT GTA AAT CAA 865                 870                 875                 880
Ala Lys Arg Leu Ser Lys Ala Arg Asn Leu Leu Val Gly Gly Asn Phe Asp Asn Leu Asp
GCG AAG CGC TTA AGC AAG GCG CGT AAT CTC CTG GTA GGC AAT TTT GAT AAC TTG GAT 885                 890                 895                 900
Ala Trp Tyr Arg Gly Arg Asn Val Asn Val Val Ser Asn His Glu Leu Leu Lys Ser Asp
GCT TGG TAT AGA GGA AGA AAT GTA AAC GTA TCT AAT CAC GAA CTG TTG AAG AGT GAT 905                 910                 915                 920
His Val Leu Leu Pro Pro Pro Gly Leu Ser Tyr Ile Phe Gln Lys Val Glu Glu
CAT GTA TTA TTA CCA CCA CCA GGA TTG TCT TAT ATT TTC CAA AAA GTG GAG GAA 925                 930                 935                 940
Ser Lys Leu Lys Arg Asn Thr Arg Tyr Thr Val Ser Gly Phe Ile Ala His Ala Thr Asp
TCT AAA TTA AAA CGA AAT ACA CGT TAT ACG GTT TCT GGA TTT ATT GCG CAT GCA ACA GAT 945                 950                 955                 960
Leu Glu Ile Val Val Ser Arg Tyr Gly Gln Glu Ile Lys Lys Val Val Gln Val Pro Tyr
TTA GAA ATT GTG GTT TCT CGT TAT GGG CAA GAA ATA AAG AAA GTG GTG CAA GTT CCT TAT
```

Figure 6G

```
Gly Glu Ala Phe Pro Leu Thr Ser Ser Gly Pro Val Cys Cys Ile Pro His Ser Thr Ser
GGA GAA GCA TTC CCA TTA ACA TCA AGT GGA CCA GTT TGT TGT ATC CCA CAT TCT ACA AGT
        965                 970                 975                 980

Asn Gly Thr Leu Gly Asn Pro His Phe Ser Tyr Ser Ile Phe Asp Val Gly Ala Leu Asp
AAT GGA ACT TTA GGC AAT CCA CAT TTC AGT TAC AGT ATT GAT GTA GGT GCA TTA GAT
        985                 990                 995                 1000

Val Asp Thr Asn Pro Gly Ile Glu Phe Gly Leu Arg Ile Val Asn Pro Thr Gly Met Ala
GTA GAC ACA AAC CCT GGT ATT GAA TTC GGT CTT CGT ATT GTA AAT CCA ACT GGA ATG GCA
        1005                1010                1015                1020

Arg Val Ser Asn Leu Glu Ile Arg Glu Asp Arg Pro Leu Ala Ala Asn Glu Ile Arg Gln
CGC GTA AGC AAT TTG GAA ATT CGT GAA GAT CGT CCA TTA GCA GCA AAT GAA ATA CGA CAA
        1025                1030                1035                1040

Val Gln Arg Val Ala Arg Asn Trp Arg Thr Glu Tyr Glu Lys Arg Ala Glu Val Thr
GTA CAA CGT GTC GCA AGA AAT TGG AGA ACC GAG TAT GAG AAA CGT GCG GAA GTA ACA
        1045                1050                1055                1060

Ser Leu Ile Gln Pro Val Ile Asn Arg Ile Asn Gly Leu Tyr Asp Asn Gly Asn Trp Asn
AGT TTA ATT CAA CCT GTT ATC AAT CGA ATC AAT GGA TTG TAT GAC AAT GGA AAT TGG AAC
        1065                1070                1075                1080

Gly Ser Ile Arg Ser Asp Ile Ser Tyr Gln Asn Ile Asp Ala Ile Val Leu Pro Thr Leu
GGT TCT ATT CGT TCA GAT ATT TCG TAT CAG AAT ATA GAC GCG ATT GTA TTA CCA ACG TTA
        1085                1090                1095                1100
```

Figure 6H

```
Pro Lys Leu Arg His Trp Phe Met Ser Asp Arg Phe Ser Glu Gln Gly Asp Ile Met Ala
CCA AAG TTA CGC CAT TGG TTT ATG TCA GAT AGA TTT AGT GAA CAA GGA GAT ATC ATG GCT
    1105                    1110                   1115                    1120

Ser Leu Ile Gln Pro Val Ile Asn Arg Ile Asn Gly Leu Tyr Asp Asn Gly Asn Trp Asn
AGT TTA ATT CAA CCT GTT ATC AAT CGA ATC AAT GGA TTG TAT GAC AAT GGA AAT TGG AAC
    1065                    1070                   1075                    1080

Gly Ser Ile Arg Ser Asp Ile Ser Tyr Gln Asn Ile Asp Ala Ile Val Leu Pro Thr Leu
GGT TCT ATT CGT TCA GAT ATT TCG TAT CAG AAT ATA GAC GCG ATT GTA TTA CCA ACG TTA
    1085                    1090                   1095                    1100

Pro Lys Leu Arg His Trp Phe Met Ser Asp Arg Phe Ser Glu Gln Gly Asp Ile Met Ala
CCA AAG TTA CGC CAT TGG TTT ATG TCA GAT AGA TTT AGT GAA CAA GGA GAT ATC ATG GCT
    1105                    1110                   1115                    1120

Lys Phe Gln Gly Ala Leu Asn Arg Ala Tyr Ala Gln Leu Glu Gln Asn Thr Leu Leu His
AAA TTC CAA GGT GCA TTA AAT CGT GCG TAT GCA CAA CTG GAA CAA AAT ACG CTT CAT
    1125                    1130                   1135                    1140

Asn Gly His Phe Thr Lys Asp Ala Ala Asn Trp Thr Val Glu Gly Asp Ala His Gln Val
AAT GGT CAT TTT ACA AAA GAT GCA GCC AAT TGG ACG GTA GAA GGC GAT GCA CAT CAG GTA
    1145                    1150                   1155                    1160

Val Leu Glu Asp Gly Lys Arg Val Leu Arg Leu Pro Asp Trp Ser Ser Ser Val Ser Gln
GTA TTA GAA GAT GGT AAA CGT GTA TTA CGA TTG CCA GAT TGG TCG AGT TCT GTG TCT CAA
    1165                    1170                   1175                    1180
```

Figure 6I

```
                                       1185                    1190                    1195                    1200
Thr Ile Glu Ile Glu Asn Phe Asp Pro Asp Lys Glu Tyr Gln Leu Val Phe His Gly Gln
ACG ATT GAA ATC GAG AAT TTT GAT CCA GAT AAA GAA TAT CAA TTA GTA TTT CAT GGG CAA 1205                    1210                    1215                    1220
Gly Gly Thr Val Thr Leu Glu His Gly Glu Thr Lys Tyr Ile Glu Thr His Thr
GGA GGA ACG GTT ACG TTG GAG CAT GGA GAA ACA AAA TAT ATA GAA ACG CAT ACA 1225                    1230                    1235                    1240
His His Phe Ala Asn Phe Thr Ser Gln Arg Gln Gly Leu Thr Phe Glu Ser Asn Lys
CAT CAT TTT GCG AAT TTT ACA ACT TCT CAA CGT CAA GGA CTC ACG TTT GAA TCA AAT AAA 1245                    1250                    1255                    1260
Val Thr Val Thr Ile Ser Ser Glu Asp Gly Glu Phe Leu Val Asp Asn Ile Ala Leu Val
GTG ACA GTG ACC ATT TCT TCA GAA GAT GGA GAA TTC TTA GTG GAT AAT ATT GCG CTT GTA 1265                    1270                    1275                    1280
Glu Ala Pro Leu Pro Thr Asp Asp Gln Asn Ser Glu Gly Asn Thr Ala Ser Ser Thr Asn
GAA GCT CCT CTT CCT ACA GAT GAC CAA AAT TCT GAG GGA AAT ACG GCT TCC AGT ACG AAT

1285
Ser Asp Thr Ser Met Asn Asn Asn Gln
AGC GAT ACA AGT ATG AAC AAC AAT CAA
```

Figure 6J

PS176 GENE ENCODING NEMATODE-ACTIVE TOXIN CLONED FROM A BACILLUS THURINGIENSIS ISOLATE

CROSS-REFERENCE TO A RELATED APPLICATION

This is a division of application Ser. No. 07/557,246, filed Jul. 24, 1990, now U.S. Pat. No. 5,281,530, which is a continuation-in-part of Ser. No. 07/535,810, filed Jun. 11, 1990, now abandoned, which is a continuation-in-part of Ser. No. 07/084,653, filed Aug. 12, 1987, now U.S. Pat. No. 4,948,734.

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice*, Vol 2:423–432 [Herd, R. P., eds.] W. B. Saunders, New York). There are more than 100,000 described species of nematodes.

The bacterium *Bacillus thuringiensis* (*B.t.*) produces a δ-endotoxin polypeptide that has been shown to have activity against a rapidly growing number of insect species. The earlier observations of toxicity only against lepidopteran insects have been expanded with descriptions of *B.t.* isolates with toxicity to dipteran and coleopteran insects. These toxins are deposited as crystalline inclusions within the organism. Many strains of *B.t.* produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239–244, 1985) have reported that *B.t. kurstald* and *B.t. israelensis* were toxic in vitro to eggs of the nematode *Trichostrongylus colubriformis*. In addition, 28 other *B.t.* strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such effective means would employ biological agents. In parent pending application Ser. No. 084,653, there are disclosed novel isolates of *Bacillus thuringiensis* having activity against nematodes. We have now isolated, unexpectedly and advantageously, four genes encoding novel nematicidal δ-endotoxins from one of the *B.t.* isolates which was named *B.t.* PS17. Prior to successfully completing this invention, we could not predict with any reasonable degree of certainty that we could isolate a gene encoding a nematicidal toxin because of the complexity of the microbial genome. The fact that more than one gene was successfully cloned is completely unexpected.

BRIEF SUMMARY OF THE INVENTION

The subject invention concerns four genes cloned from a novel *Bacillus thuringiensis* isolate designated *B.t.* PS17. The genes designated PS17d, PS17b, PS17a and PS17e, encode *Bacillus thuringiensis* δ-endotoxins which have nematicidal activity. The genes can be transferred to suitable hosts via a recombinant DNA vector.

BRIEF DESCRIPTION OF THE DRAWINGS

FIG. 1A–C discloses the amino acid sequence of the novel toxin encoded by PS17a.

FIG. 2A–D discloses the nucleotide sequence of PS17a.

FIG. 3A–L is a composite of FIGS. 1 and 2.

FIG. 4A–C discloses the nucleotide sequence of PS17b.

FIG. 5A–B discloses the amino acid sequence of the novel toxin encoded by PS17b.

FIG. 6A–J is a composite of FIGS. 4 and 5.

DETAILED DISCLOSURE OF THE INVENTION

The novel toxin genes of the subject invention were obtained from a nematode-active *B. thuringiensis* (*B.t.*) isolate designated PS17. A subculture of *B.t.* PS17 and the *E. coli* host harboring the toxin genes of the invention were deposited in the permanent collection of the Northern Research Laboratory, U.S. Department of Agriculture, Peoria, Ill., USA. The accession numbers are as follows:

*B.t.*PS17—NRRL B-18243—Deposited on Jul. 28, 1987.

*E. coli* NM522(pMYC1627)—NRRL B-18651—Deposited on May 11, 1990.

*E. coli* NM522(pMYC1628)—NRRL B-18652—Deposited on May 11, 1990.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel *B.t.* genes of the invention encode toxins which show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes wide-spread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxins encoded by the novel *B.t.* genes of the invention are useful as nematocides for the control of soil nematodes and plant parasites selected from the genera Bursaphalenchus, Criconemella, Ditylenchus, Globodera, Helicotylenchus, Heterodera, Melodiogyne, Pratylenchus, Radopholus, Rotelynchus, or Tylenchus.

Alternatively, because some plant parasitic nematodes are obligate parasites, genes coding for nematocidal *B.t.* toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387-399, 1984).

The *B.t.* toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, nagnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraruminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

The toxin genes of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophlius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are known and available for introducing the *B.t.* genes expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomcyes sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* nematicidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1–95% by weight of the nematicide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

Example 1—Culturing *B.t.* PS17, NRRL B-18243

A subculture of *B.t.* PS17, NRRL B-18243, can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

Example 2—Purification and N-Terminal Sequncing of *B.t.* Isolate PS17

The *Bacillus thuringiensis* (*B.t.*) isolate used as the source of nematicidal toxin protein of the subject invention is identified as *B.t.* strain PS17. The culture was grown using standard media and fermentation techniques well known in the art. The toxin protein inclusions were harvested by standard sedimentation centrifugation. The recovered protein inclusions were partially purified by sodium bromide (28–38%) isopycnic gradient centrifugation (Pfannenstiel, M. A., E. J. Ross, V. C. Kramer, and K. W. Nickerson [1984] FEMS Microbiol. Lett. 21:39). Thereafter the individual toxin proteins were resolved by solubilizing the crystalline protein complex in an alkali buffer and fractionating the individual proteins by DEAE-sepharose CL-6B (Sigma Chem. Co., St. Louis, Mo.) chromatography by stepwise increments of increasing concentrations of an NaCl-containing buffer (Reichenberg, D., in *Ion Exchangers in Organic and Biochemistry* [C. Calmon and T. R. E. Kressman, eds.], Interscience, New York, 1957). Fractions containing protein toxic for the nematode *Caenorhabditis elegans* (CE), were bound to PVDF membrane (Millipore, Bedford, Mass.) by western blotting techniques (Towbin, H., T. Staehelin, and K. Gordon [1979] Proc. Natl. Acad. Sci. USA 76:4350) and the N-terminal amino acids were determined by the standard Edman reaction with an automated gas-phase sequenator (Hunkapiller, M. W., R. M. Hewick, W. L. Dreyer, and L. E. Hood [1983] Meth. Enzymol. 91:399). From these sequence data an oligonucleotide probe was designed by utilizing a codon frequency table assembled from available nucleotide sequence data of other *B.t.* toxin genes. The probe was synthesized on an Applied Biosystems, Inc. DNA synthesis machine.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

Example 3—Cloning of Four Novel Toxin Genes from *B.t.* PS17 and Transformation into *Escherichia coli*.

Total cellular DNA was prepared by growing the cells *B.t.* PS17 to a low optical density (OD$_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCL, 20 ram NaOAc, 2.5 mM EDTA, pH=8.0) buffered gel. A Southern blot of the gel was hybridized with a [$^{32}$P]—radiolabeled oligonucleotide probe derived from the N-terminal amino acid sequence of purified 130 kDa protein from PS17. The sequence of the oligonucleotide synthesized is (GCAATTTTAAATGAAT-TATATCC). Results showed that the hybridizing EcoRI fragments of PS17 are 5.0 kb, 4.5 kb, 2.7 kb and 1.8kb in size, presumptively identifying at least four new nematode-active toxin genes, PS17d, PS17b, PS17a and PS17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip TM ion exchange column (Schleicher and Schuel, Keene NH). The isolated Sau3A fragments were ligated into LambdaGEM-11 TM (PROMEGA). The packaged phage were plated on KW251 *E. coli* cells(PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (PS17b) or the 2.7 kb (PS17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac. The ligation mix was introduced by transformation into NM522 competent *E. coli* cells and plated on LB agar containing ampicillin, isopropyl-(Beta)-D-thiogalactoside (IPTG) and 5-Bromo-4-Chloro-3-indolyl-(Beta)-D-galactoside(X-GAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

The PS17 toxin genes were subcloned into the shuttle vector pHT3101 (Lereclus, D. et al. [1989] FEMS Microbiol. Lett. 60:211-218) using standard methods for expression in *B.t.*. Briefly, SalI fragments containing the PS17a and b toxin genes were isolated from pMYC1629 and pMYC1627, respectively, by preparative agarose gel electrophoresis, electroelution, and concentrated, as described above. These concentrated fragments were ligated into SalI-cleaved and phosphatased pHT3101. The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the PS17a and b toxin genes, respectively. These plasmids were transformed into the acrystalliferous *B.t.* strain, HD-1 cryB (Purdue University, Lafayette, Ind.), by standard electroporation techniques (Instruction Manual, Biorad, Richmond, Calif.).

Recombinant *B.t.* strains HD-1 cryB [pMYC2311] and [pMYC2309] were grown to sporulation and the proteins purified by NaBr gradient centrifugation as described above for the wild-type *B.t.* proteins.

Example 4—Activity of the *B.t.* Toxin Protein and Gene Product Against *Caenorhabditis elegans*

*Caenorhabditis elegans* (CE) was cultured as described by Simpkin and Coles (J. Chem. Tech. Biotechnol. 31:66–69, 1981) in corning (Corning Glass Works, Corning, N.Y.) 24-well tissue culture plates containing 1 ml S-basal media, 0.5 mg ampicillin and 0.01 mg cholesterol. Each well also contained ca. $10^8$ cells of *Escherichia coli* strain OP-50, a uracil auxotroph. The wells were seeded with ca. 100–200 CE per well and incubated at 20° C. Samples of protein (obtained from the wild type *B.t.* or the recombinant *B.t.*) were added to the wells by serial dilution. Water served as the control as well as the vehicle to introduce the proteins to the wells.

Each of the wells were examined daily and representative results are as follows:

| | % KILL | | |
|---|---|---|---|
| μg toxin | pMYC2309 | pMYC2311 | PS17 |
| 100 | 25 | 50 | 75 |
| 32 | 25 | 50 | 75 |
| 10 | 50 | 25 | 50 |
| 1 | 0 | 0 | 0 |

Example 5—Activity Against the Plant Nematodes Pratylenchus spp.

The toxin encoded by *B.t.* PS17a has been found to be active against Pratylenchus spp. The activity is approximately at the same level as is disclosed in Example 4 against *C. elegans.*

Species of Pratylenchus, for example, *P. scribneri* and *P. redivivous,* are known pathogens of many economically important crops including corn, peanuts, soybean, alfalfa, beans, tomato, and citrus. These "root lesion" nematodes are the second most economically damagging genus of plant parasitic nematodes (after Meliodogyne—the "root knot" nematode), and typify the migratory endoparasites.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |

-continued

| | | | |
|---|---|---|---|
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

We claim:

1. Isolated DNA encoding a *Bacillus thuringiensis* nematicidal toxin having an amino acid sequence shown in FIG. 5.

2. Isolated DNA encoding a *Bacillus thuringiensis* nematicidal toxin, said isolated DNA having a nucleotide sequence shown in FIG. 4.

3. A prokaryotic or eukaryotic microorganism host cell, stably transformed with a DNA transfer vector comprising a gene selected from the group consisting of genes designated *B.t.* PS17b.

4. A transformed prokaryotic host according to claim 3, selected from the group consisting of *Escherichia coli* (NM522) (pMYC1628), having the identifying characteristics of NRRL B-18652, and *Escherichia coli* (NM522) (pMYC2309).

* * * * *

UNITED STATES PATENT AND TRADEMARK OFFICE
CERTIFICATE OF CORRECTION

PATENT NO. : 5,426,049
DATED : Jun. 20, 1995
INVENTOR(S) : August J. Sick, et al It is certified that error appears in the above-indentified patent and that said Letters Patent is hereby corrected as shown below:

On title page, item [54] and
Column 1, line 2 (Title): Delete "PS176" and insert --PS17B--

Column 1, line 48: Delete "Kurstald" and insert --Kurstaki--.

Column 2, line 6: Delete "B.t., PS17" and insert --B.t. PS17--.

Column 8, line 51: Delete "20 ram" and insert --20 mM--.

Column 12, line 24: Delete "thuringiensis;" and insert --thuringiensis--.

Signed and Sealed this

Nineteenth Day of September, 1995

Attest:

BRUCE LEHMAN

Attesting Officer         Commissioner of Patents and Trademarks